US009518044B2

(12) United States Patent
Jiang et al.

(10) Patent No.: US 9,518,044 B2
(45) Date of Patent: Dec. 13, 2016

(54) PROSTAGLANDIN RECEPTOR EP2 ANTAGONISTS, DERIVATIVES, COMPOSITIONS, AND USES RELATED THERETO

(75) Inventors: Jianxiong Jiang, Decatur, GA (US); Thota Ganesh, Alpharetta, GA (US); Yuhong Du, Atlanta, GA (US); Pahk Thepchatri, Atlanta, GA (US); Yi Quan, Decatur, GA (US); Ray J. Dingledine, Norcross, GA (US)

(73) Assignee: Emory University, Atlanta, GA (US)

( * ) Notice: Subject to any disclaimer, the term of this patent is extended or adjusted under 35 U.S.C. 154(b) by 196 days.

(21) Appl. No.: 14/126,689

(22) PCT Filed: Jun. 19, 2012

(86) PCT No.: PCT/US2012/043116
§ 371 (c)(1),
(2), (4) Date: Feb. 20, 2014

(87) PCT Pub. No.: WO2012/177618
PCT Pub. Date: Dec. 27, 2012

(65) Prior Publication Data
US 2014/0179750 A1   Jun. 26, 2014

Related U.S. Application Data

(60) Provisional application No. 61/498,866, filed on Jun. 20, 2011.

(51) Int. Cl.
*C07D 405/12* (2006.01)
*A61K 31/404* (2006.01)
(Continued)

(52) U.S. Cl.
CPC .......... *C07D 405/12* (2013.01); *A61K 31/404* (2013.01); *A61K 31/4184* (2013.01); *C07D 209/08* (2013.01); *C07D 235/08* (2013.01)

(58) Field of Classification Search
CPC ... C07D 405/12; C07D 235/08; C07D 209/08; A61K 31/404; A61K 31/4184
See application file for complete search history.

(56) References Cited

U.S. PATENT DOCUMENTS

2009/0163545 A1   6/2009   Goldfarb

FOREIGN PATENT DOCUMENTS

| CN | 101157668 | 4/2008 |
|----|-----------|--------|
| JP | 2008115088 | 5/2008 |

(Continued)

OTHER PUBLICATIONS

Battaglia et al. "Indole amide derivatives: synthesis, structure—activity relationships and molecular modelling studies of a new series of histamine H1-receptor antagonists" Eur J Med Chem., Feb. 1999; 34(2): 93-105.

(Continued)

*Primary Examiner* — Savitha Rao
*Assistant Examiner* — Angela Brown-Pettigrew
(74) *Attorney, Agent, or Firm* — Emory Patent Group

(57) ABSTRACT

The present invention is directed to compounds of Formula IC:

(Continued)

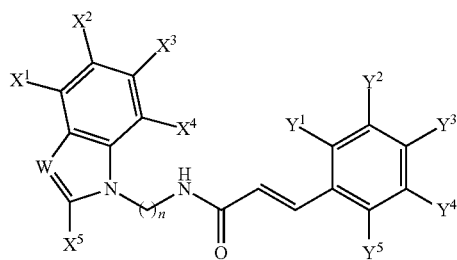

wherein the substituents are described herein. These compounds and their pharmaceutically acceptable salts thereof are prostaglandin receptor EP2 antagonists.

3 Claims, 10 Drawing Sheets

(51) Int. Cl.
*A61K 31/4184* (2006.01)
*C07D 209/08* (2006.01)
*C07D 235/08* (2006.01)

(56) References Cited

FOREIGN PATENT DOCUMENTS

| WO | 9931064 | 6/1999 | |
|---|---|---|---|
| WO | 2004035525 | 4/2004 | |
| WO | WO 2004/035525 | * | 4/2004 |
| WO | 2008152099 | | 12/2008 |
| WO | 2010012396 | | 2/2010 |
| WO | 2010012397 | | 2/2010 |

OTHER PUBLICATIONS

Fu et al. "EP2 Receptor Signaling Regulates Microglia Death" Mol Pharmacol, Jul. 2015; 88: 161-170.
Ganesh et al. "Development of second generation EP2 antagonists with high selectivity" Eur J Med Chem., Jul. 23, 2014; 82: 521-535.
Ganesh et al. "Lead Optimization Studies of Cinnamic Amide EP2 Antagonists" J. Med. Chem., 2014; 57(10): 4173-4184.
Jiang et al. "Small molecule antagonist reveals seizure-induced mediation of neuronal injury by prostaglandin E2 receptor subtype EP2" Proc Natl Acad Sci U S A, 2012; 109(8): 3149-3154.
Jiang et al. "Therapeutic window for cyclooxygenase-2 related anti-inflammatory therapy after status epilepticus" Neurobiology of Disease, 2015; 76: 126-136.
Liang et al. "Deletion of the Prostaglandin E2 EP2 Receptor Reduces Oxidative Damage and Amyloid Burden in a Model of Alzheimer's Disease" The Journal of Neuroscience, 2005; 25(44): 10180-10187.
Rojas et al. "Inhibition of the prostaglandin EP2 receptor is neuroprotective and accelerates functional recovery in a rat model of organophosphorus induced status epilepticus" Neuropharmacology, Jun. 2015 ; 93: 15-27.
Yang "Altered hippocampal long-term synaptic plasticity in mice deficient in the PGE2 EP2 receptor" J Neurochem 2009; 108: 295-304.

* cited by examiner

PROSTAGLANDIN RECEPTOR EP2 ANTAGONISTS, DERIVATIVES, COMPOSITIONS, AND USES RELATED THERETO

CROSS REFERENCE TO RELATED APPLICATIONS

This application claims priority to U.S. Provisional Application No. 61/498,866 filed Jun. 20, 2011, hereby incorporated by reference in its entirety.

STATEMENT REGARDING FEDERALLY FUNDED RESEARCH

This invention was made with government support under Grants 1U54 HG003918 and 1U01 NS058158 awarded by the National Institutes of Health. The government has certain rights in the invention.

BACKGROUND

Status epilepticus is a condition in which the brain is in a state of persistent seizure. There is evidence that 30-60 minutes of persistent seizure is sufficient to damage neurons and that such a seizure is unlikely to self-terminate. Status epilepticus survivors may die soon after or have severe functional impairments accompanied by neuroinflammation. Longer seizure duration, cerebral insult, and refractory convulsive status epilepticus were strongly associated with poor outcomes suggesting a role for early neuroprotective strategies. See Legriel et al., Critical Care Medicine, 2010, 38 (12):2295-2303. Thus, there is a need to identify improved methods for treating or preventing patients recovering from prolonged seizures.

Cyclooxygenase-2 (COX-2), the inducible isoform of COX, is rapidly upregulated in damaged tissue, for example in the central nervous system (CNS) after a seizure or cerebral ischemia. In the CNS, COX-2 induction overall contributes to neuroinflammation and neurodegeneration by producing prostaglandins. In the periphery COX-2 induction has both beneficial and harmful consequences. Pharmacological inhibition of COX can provide relief from the symptoms of inflammation and pain. Current non-steroidal anti-inflammatory drugs (NSAIDs), such as aspirin, ibuprofen, and naproxen, exert their therapeutic effects via nonselectively inhibiting COX. However, multiple downstream COX-2 signaling pathways that promote and oppose tissue injury are complex, which suggests that modulation of a specific prostaglandin receptor could be a superior therapeutic strategy compared with blocking the entire COX-2 cascade.

Prostaglandin $E_2$ ($PGE_2$), a dominant enzymatic product of COX-2 in CNS, can activate four G protein-coupled receptors (GPCRs): EP1, EP2, EP3 and EP4. When activated by $PGE_2$, EP2 stimulates adenylate cyclase (AC) resulting in elevation of cytoplasmic cyclic AMP (cAMP) concentration, which triggers multiple downstream events mediated by protein kinase A (PKA) and exchange protein activated by cAMP (Epac).

In periphery, PGE2/EP2 signaling plays a variety of roles. For example, $PGE_2$ is a major mediator of inflammation and pain. $PGE_2$ is observed as one of the major prostanoid species in inflammatory lesions such as arthritic joints and shows pleiotropic proinflammatory actions in vitro. Direct delivery of $PGE_2$ into tissues can elicit inflammation and ablation of microsomal PGE synthase or EP2 showed reduced arthritic responses in collagen-induced arthritis. Therefore, the beneficial effect of NSAIDs could be at least partially if not fully, caused by their inhibition of $PGE_2$ production, and the PGE2/EP2 signaling pathway might induce inflammation actions observed in chronic inflammatory diseases such as rheumatoid arthritis (RA). In addition, $PGE_2$/EP2 signaling regulates UV-induced acute skin inflammation by increasing skin microenviromental blood flow, and EP2 activation by oxidized 1-palmitoyl-2-arachidonoyl-sn-glycero-3-phosphorylcholine (OxPAPC) might contribute to vascular inflammation. $PGE_2$ signaling through EP2/EP4 exacerbates symptoms of inflammation by increasing IL-23 expression and reducing IL-12/IL-27, which together causes T-cells to differentiate to Th17 effectors both in inflammatory bowel disease (colitis) and arthritis. $PGE_2$/EP2 system up-regulates a variety of inflammatory mediators including chemokines, cytokines, nitric oxide, prostaglandins, etc., to develop and maintain the inflammatory response.

In the brain, based on the phenotype of EP2 knockout mice, it appears that EP2 activation in microglia promotes inflammation and neurotoxicity in animal models of neurodegenerative diseases including Alzheimer's disease (AD), Parkinson's disease (PD), and amyotrophic lateral sclerosis (ALS). Genetic ablation of EP2 receptor reduced oxidative stress and improved cell survival, accompanied by substantial down-regulation of enzymes in glia that produce reactive oxygen species (ROS), such as inducible nitric oxide synthase (iNOS), COX-2, and NAPDH oxidase. EP2 receptor activation by $PGE_2$ upregulates iNOS/NO expression in activated astrocytes by potentiating the response to inflammatory cytokines like TNF-α and IFN-γ.

Because PGE2/EP2 signaling mediates both peripheral and neural inflammation, pharmacological targeting this pathway can have beneficial implications for the treatment of inflammatory diseases. Thus, there is a need to identify agents that can inhibit $PGE_2$/EP2 signaling.

Buchmann et al., (WO/2008/152099) report compositions for the treatment of disorders connected with the EP2 receptor. See also WO2010/012396.

SUMMARY

It has been discovered that certain compounds antagonize EP2 signaling. In some embodiments, this disclosure relates to compounds and methods of treating or preventing a related diseases or conditions comprising administering to a subject a therapeutically effective amount of pharmaceutical composition comprising a compounds disclosed herein, derivatives, or substituted compounds, e.g., compounds substituted with one or more substitutes including optional salt and prodrug forms. Typically, the compounds display selectivity in inhibiting the EP2 receptor over the EP4 receptor.

In certain embodiments, contemplated compounds include those comprising Formula I,

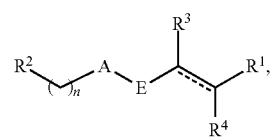

Formula I or pharmaceutically acceptable salt or prodrug thereof, wherein;

is a single or double bond;
A is $NR^5$, $CR^6R^7$, O, or S;
E is S, SO, $SO_2$, C=O, C=S, C=N—$OR^8$;
n is 1, 2, 3, or 4;
$R^1$ and $R^2$ are each, the same or different, carbocyclyl, aryl, or heterocyclyl, wherein $R^1$ and $R^2$ are optionally substituted with one or more, the same or different, $R^{10}$;
$R^3$, $R^4$, $R^5$, $R^6$, $R^7$, and $R^8$, are each, the same or different, hydrogen or alkyl, wherein $R^3$, $R^4$, $R^5$, $R^6$, $R^7$, and $R^8$ are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is aryl optionally substituted with one or more alkoxy. Typically, the aryl is phenyl and $R^2$ is a heterocyclyl optionally substituted with one or more $R^{10}$. Typically, the heterocyclyl is indolyl or benzoimidazolyl. In certain embodiments, A is NH, E is carbonyl, n is 2, $R^3$ and $R^4$ are both hydrogen, and ----- is a double bond.

In certain embodiments, the disclosure relates to pharmaceutical compositions comprising a compound of Formula IB, Formula IB or pharmaceutically acceptable salt or prodrug thereof, wherein:

A is $NR^5$, $CR^6R^7$, O, or S;
U is $CX^5$ or N;
W is $CX^6$ or N;
n is 1, 2, 3, or 4;
$R^1$ is carbocyclyl, aryl, or heterocyclyl, wherein $R^1$ is optionally substituted with one or more, the same or different, $R^{10}$;
$R^5$, $R^6$, and $R^7$, are each, the same or different, hydrogen or alkyl, wherein $R^5$, $R^6$, and $R^7$ are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamine, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2.

In certain embodiments, W is N and U is $CX^5$, wherein $X^5$ is an optionally substituted alkyl, or W is CH and U is $CX^5$, wherein $X^5$ is an optionally substituted alkyl.

In certain embodiments, $X^5$ is not methyl.

In certain embodiments, $R^1$ is phenyl substituted with one or more halogen and alkoxy.

In certain embodiments, $R^1$ is phenyl substituted with one or more halogen, alkyl, or alkoxy.

In certain embodiments, U is $CX^5$, wherein $X^5$ is alkyl substituted with one or more halogen and alkoxy.

The compounds can be combined with one or more pharmaceutically acceptable excipients to form a pharmaceutical composition. Example excipients include diluent, carrier or filler. The compositions can be formulated for enteral, parenteral, topical, transdermal, or pulmonary administration. The compounds can be formulated for immediate release, controlled release, and combinations thereof. Examples of controlled release formulations include delayed release, extended release, pulsatile release, and combinations thereof.

The compounds described herein can be used to treat a variety of diseases or conditions related to a EP2 receptor including, but not limited to, brain injury, neuropathic pain, hypertension, ischemic or hemorrhagic injury, neuroinflammation after a seizure, endometriosis, cancer, inflammatory bowel disease (colitis), arthritis/rheumatoid arthritis, skin inflammation, vascular inflammation, Alzheimer's disease (AD), Parkinson's disease (PD), amyotrophic lateral sclerosis (ALS), kidney disease/transplant rejection, atherosclerosis, ischaemic heart disease, acne vulgaris, asthma, chronic prostatitis, glomerulonephritis, hypersensitivities, pelvic inflammatory disease, sarcoidosis, vasculitis, interstitial cystitis, and autoimmune diseases.

In certain embodiments, the compounds or compositions are administered at about 0.5, 1, 2, 3, 4, or 5 hours after a subject has stopped having a seizure, e.g., because the subject was administered an anticonvulsant or an anesthetic.

In certain embodiments, the disclosure relates to the use of a compound as described herein in the production of a medicament for the treatment of a disease or condition related to a EP2 receptor. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

In certain embodiments, the disclosure relates to method of making compounds disclosed herein by mixing starting materials and reagents disclosed herein under conditions such that the compounds are formed.

DETAILED DESCRIPTION

Figure 1:
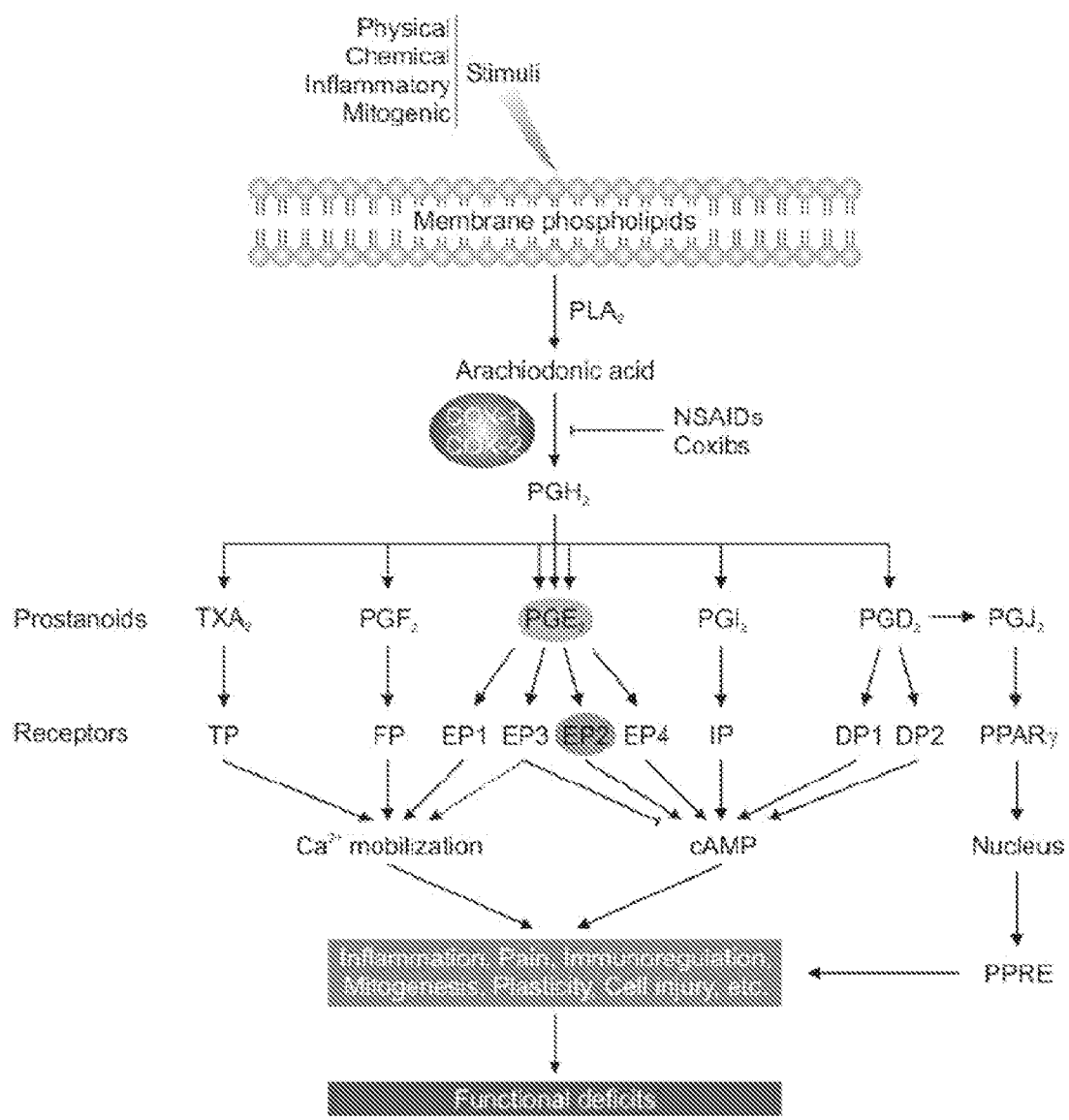
FIG. 1 illustrates the COX-2 signaling pathways. In response to a variety of stimuli, arachiodonic acid (AA) is released from membrane phospholipids by the enzyme phospholipase A2 (PLA2), and then converted to unstable intermediate prostaglandin $H_2$ ($PGH_2$) by cyclooxygenase (COX), which has two forms: COX-1 and COX-2. Most non-steroidal anti-inflammatory drugs (NSAIDs) act as non-selective inhibitors of COX, whereas certain compounds selectively inhibit COX-2. $PGH_2$ is converted to prostanoids by tissue-specific prostanoid synthases. Typically an individual cell will express a limited number of prostanoids and, therefore prostanoids. These bioactive lipids activate a number of membrane-bound G protein-coupled receptors to mediate multiple physiological effects including inflammation, pain, immunoregulation, mitogenesis, plasticity, cell injury, etc., resulting in functional deficits. Nuclear signaling via COX-2 can occur via the PGJ2 metabolite of PGD2 and PPARγ.
Figure 2:
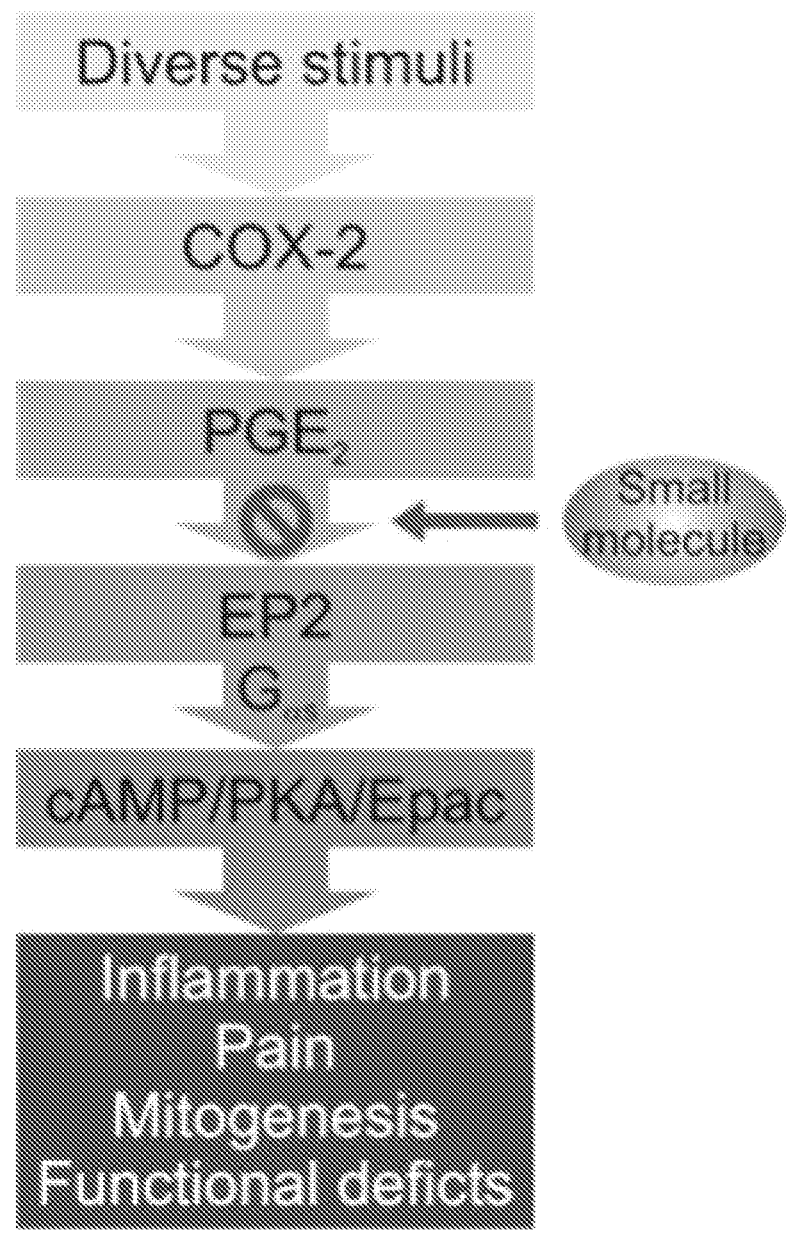
FIG. 2 illustrates how a molecule that is a competitive blocker or negative modulator of EP2 receptor could provide neuroprotection against chronic inflammation in damaged neuronal tissue.
Figure 3:
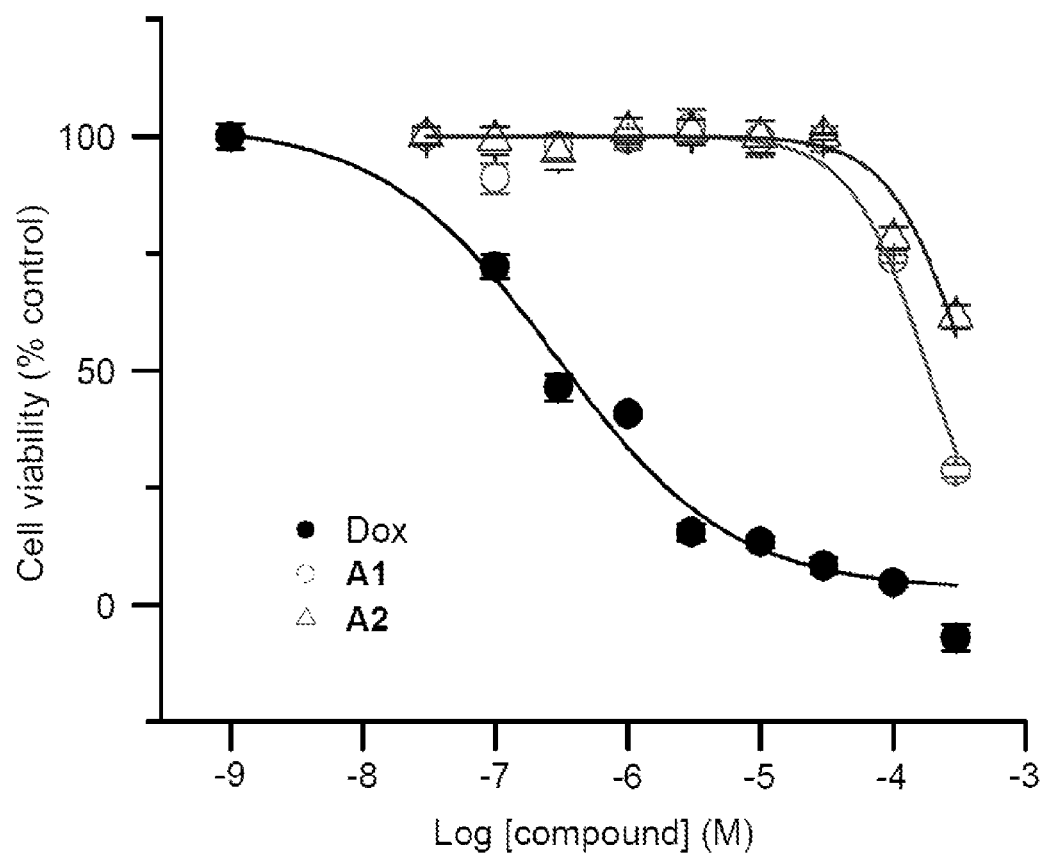
FIG. 3 shows data on the cytotoxicity of certain compounds. Cytotoxicity of the test compounds was assessed in C6G cells with the CellTiter-Glo luminescent cell viability assay. A1, $CC_{50}$=172 μM; A2, $CC_{50}$=397 μM; doxorubicin as positive control, CC50=0.2 μM.
Figure 4:
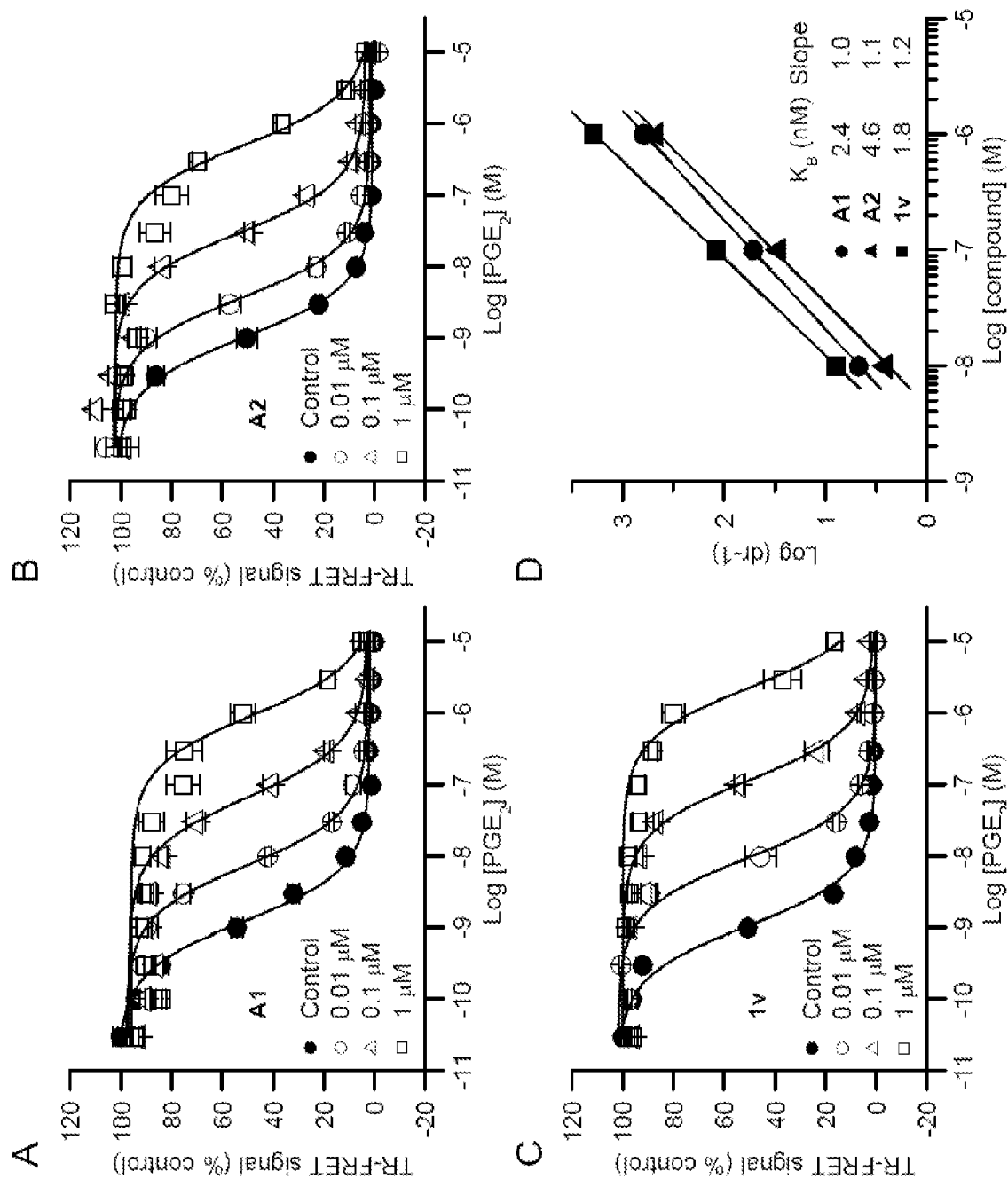
FIG. 4 shows data on the competitive antagonism on EP2 receptor by hit compounds. (A-C) Hit compounds A1, A2, and analog compound Iv showed inhibition of $PGE_2$-induced EP2 receptor activation in a concentration-dependent manner. (D) Schild regression analysis was performed to elucidate the modality of antagonism from these compounds. Data are plotted as log(dr−1) on log $X_B$. Equation: $\log(dr-1)=\log X_B-\log K_B$, dose ratio (dr)=fold shift in $PGE_2$ $EC_{50}$, $X_B$=[compound], $K_B$=equilibrium dissociation constant for the antagonist-receptor complex. Compounds A1, A2, and 1v displayed a competitive antagonism mode of action on EP2 receptor shown by Schild plots. $K_B$: 2.4, 4.6, and 1.8 nM; Slopes: 1.0, 1.1, and 1.2 for A1, A2, and 1v, respectively.
Figure 5:
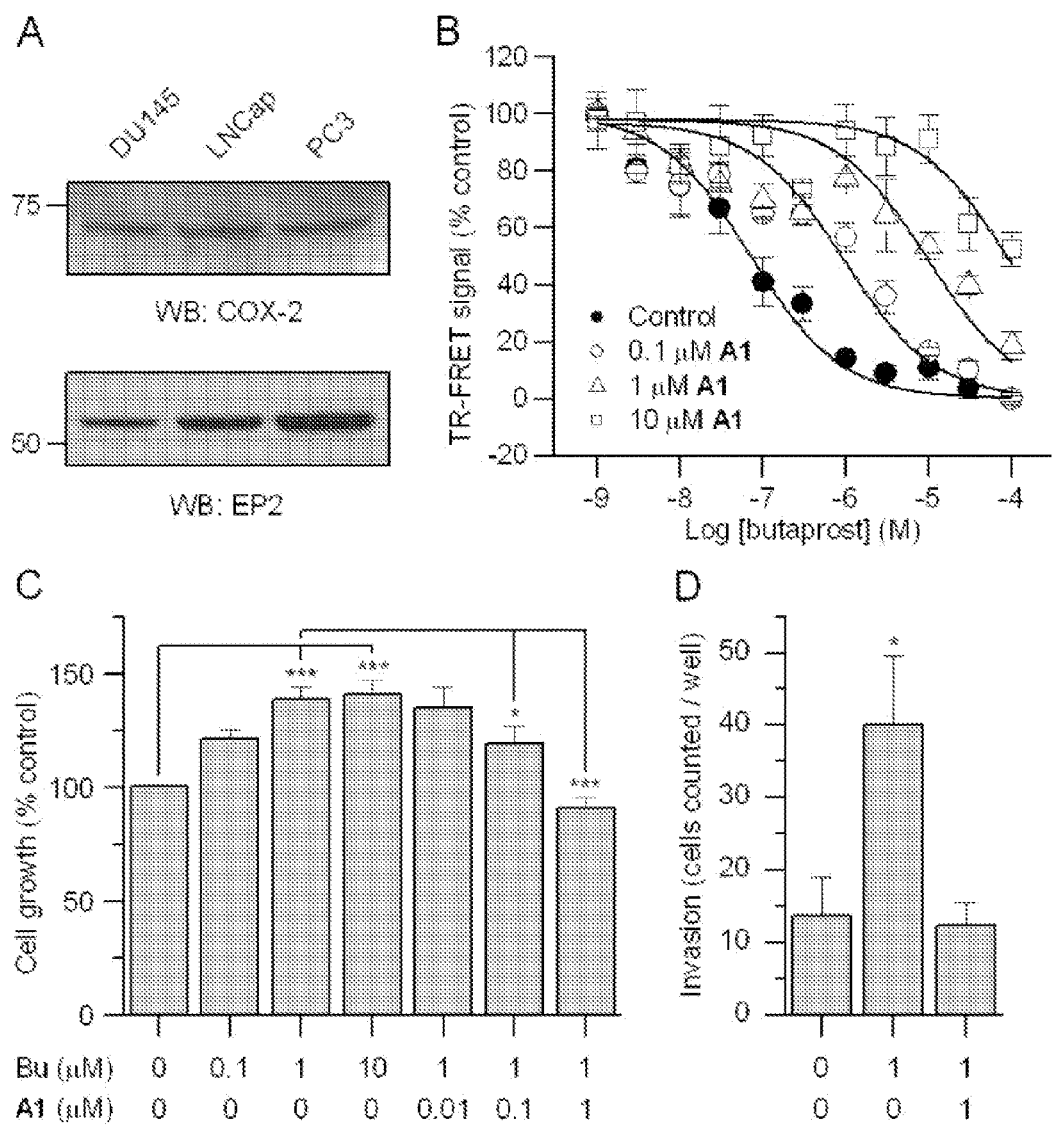
FIG. 5 shows data suggesting that EP2 antagonist compounds can suppress EP2-regulated cancer cell proliferation and invasion. (A) Relative expression of COX-2 and EP2 receptor in prostate cancer cell lines: DU145, LNCap and PC3, determined by Western blot. All cell lines express a low basal level of COX-2. PC3 cells express a substantially higher level of EP2 than DU145 and LNCap cells. 50 μg proteins for each sample were loaded for SDS-PAGE. (B) Compound A1 showed robust competitive inhibition of butaprost-induced cAMP accumulation in PC3 cells in a concentration-dependent manner. The $K_B$ of A1 in this assay was 18.1 nM. (C) EP2 activation by butaprost promoted PC3 cell growth, measured by MTT cell proliferation assay, which was attenuated by treatment with compound A 1 in a concentration-dependent manner. (D) Compound A1 blocked the PC3 cell invasion promoted by EP2 activation. Butaprost (1 μM) treatment significantly increased the number of cells that moved across the filter coated with Matrigel, which was blocked by cotreatment of compound A1 (1 μM).
Figure 6:
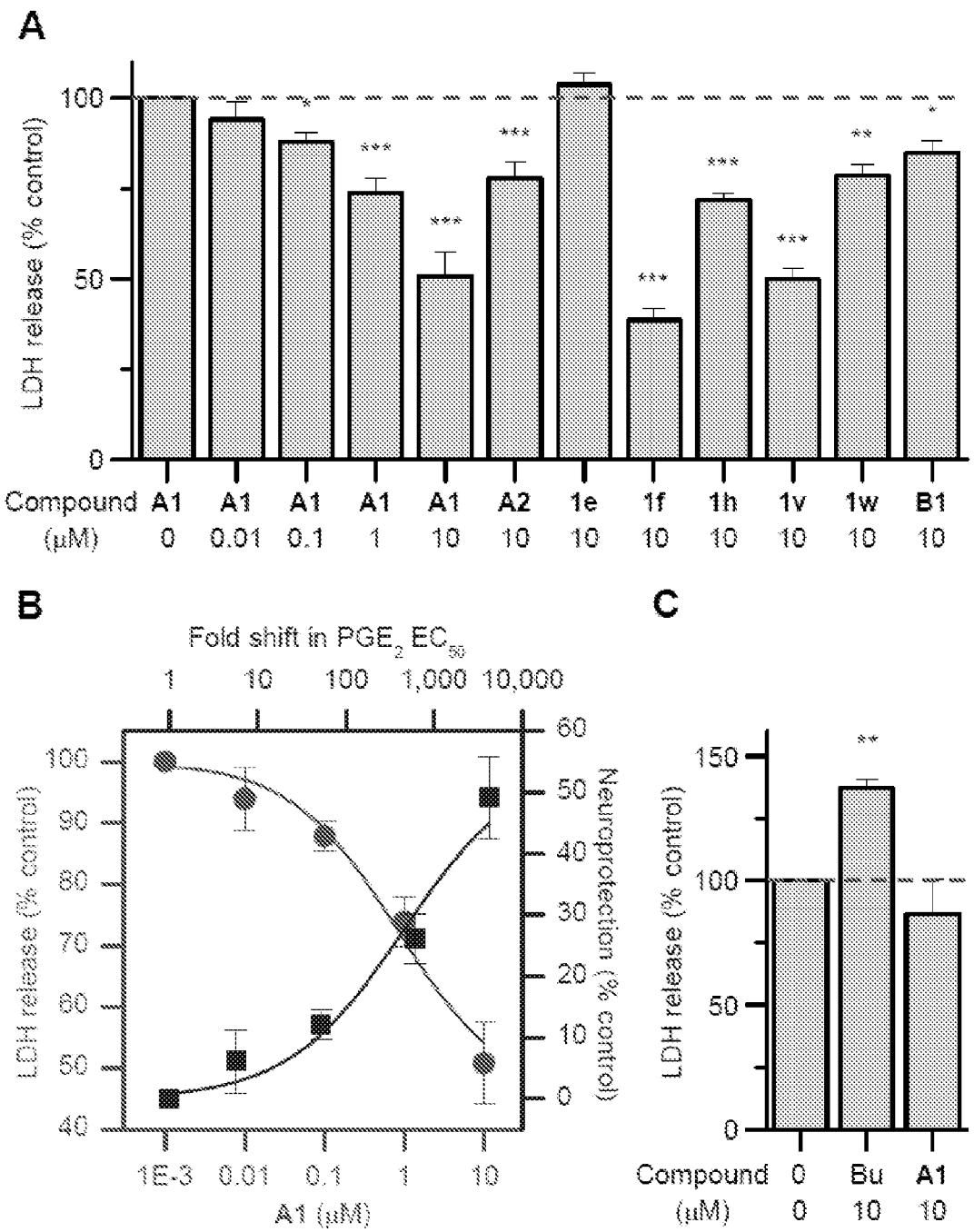
FIG. 6 shows data suggesting EP2 inhibition is neuroprotective in vitro. (A) NMDA induced lactate dehydrogenase (LDH) release in dissociated culture from rat hippocampus (DIV13-15), which was attenuated by treatment with EP2 antagonist compounds (0.01-10 μM) in a concentration-dependent manner. The NMDA-induced LDH release was reduced to 94.0, 87.8, 73.9, and 50.8% of control by 0.01, 0.1, 1, and 10 μM compound A1, respectively. The NMDA-induced LDH release was also reduced to 77.8, 38.5, 72.0, 49.9, 78.4, and 84.7% by compounds A2, 1f, 1h, 1v, 1w, and B1 (all 10 μM), respectively, but not by inactive analog 1e (10 μM). (B) Compound A1 $EC_{50}$ for the reduction of NMDA-induced LDH release was 0.80 μM (red curve). About 450-fold rightward shift in the $PGE_2$ concentration-response curve was required to yield half-maximal neuroprotection by the EP2 inhibition (blue curve). (C) LDH release in rat microglia-enriched cultures was increased to 138% by butaprost (10 μM), but reduced to 86.5% by compound A1 (10 μM), compared to control.
Figure 7:
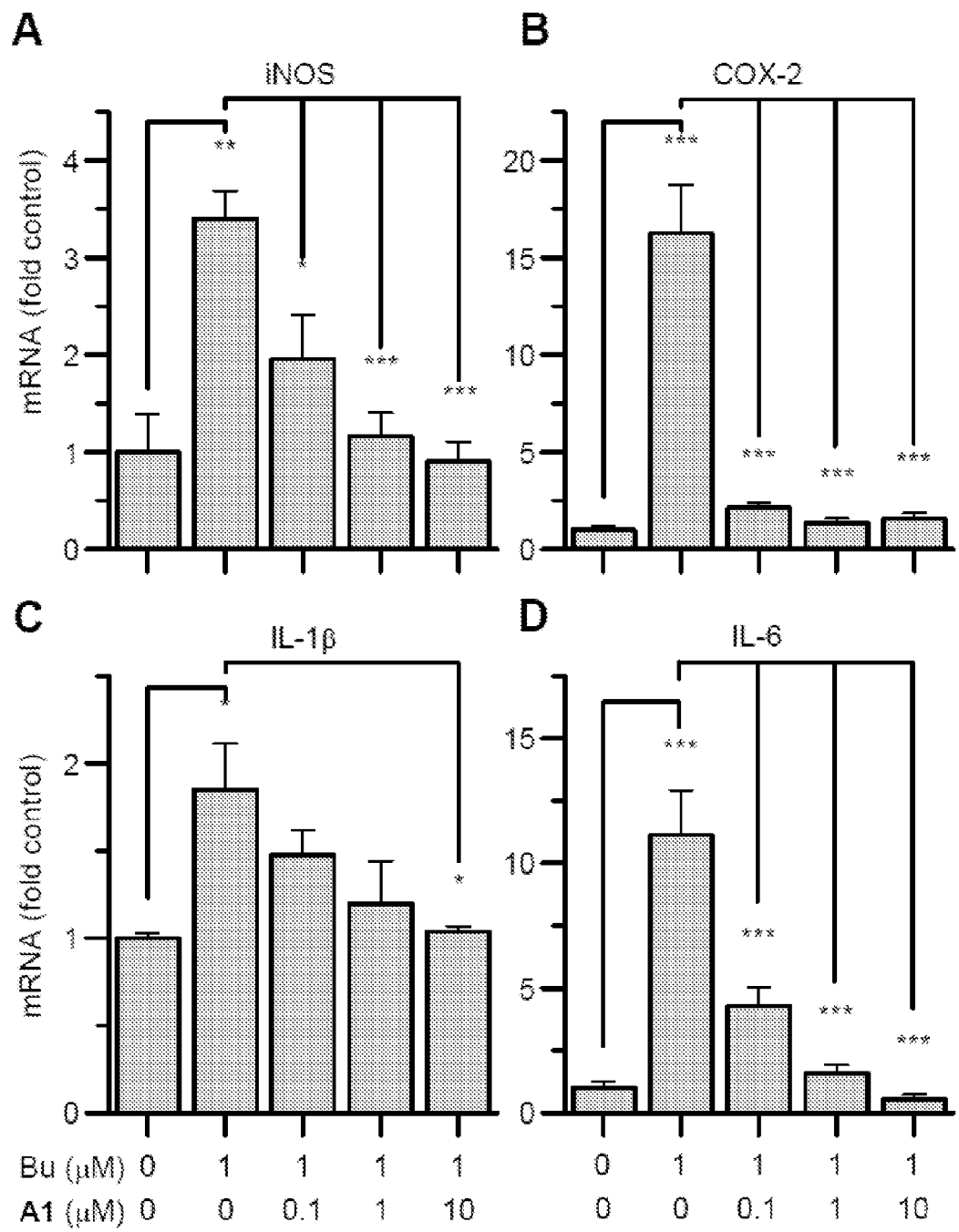
FIG. 7 shows data suggesting EP2 activation induces microglial activation. (A-D) EP2 activation in microglia by butaprost (1 μM) induced expression of inflammatory mediators: iNOS, COX-2, IL-1β and IL-6 by 3.4-, 16.3-, 1.8- and 11.1-fold, respectively, measured by quantitative real-time polymerase chain reaction (qRT-PCR). The upregulation of these inflammatory mediators was attenuated by compound A1 (0.1-10 μM) in a concentration-dependent manner.
Figure 8:
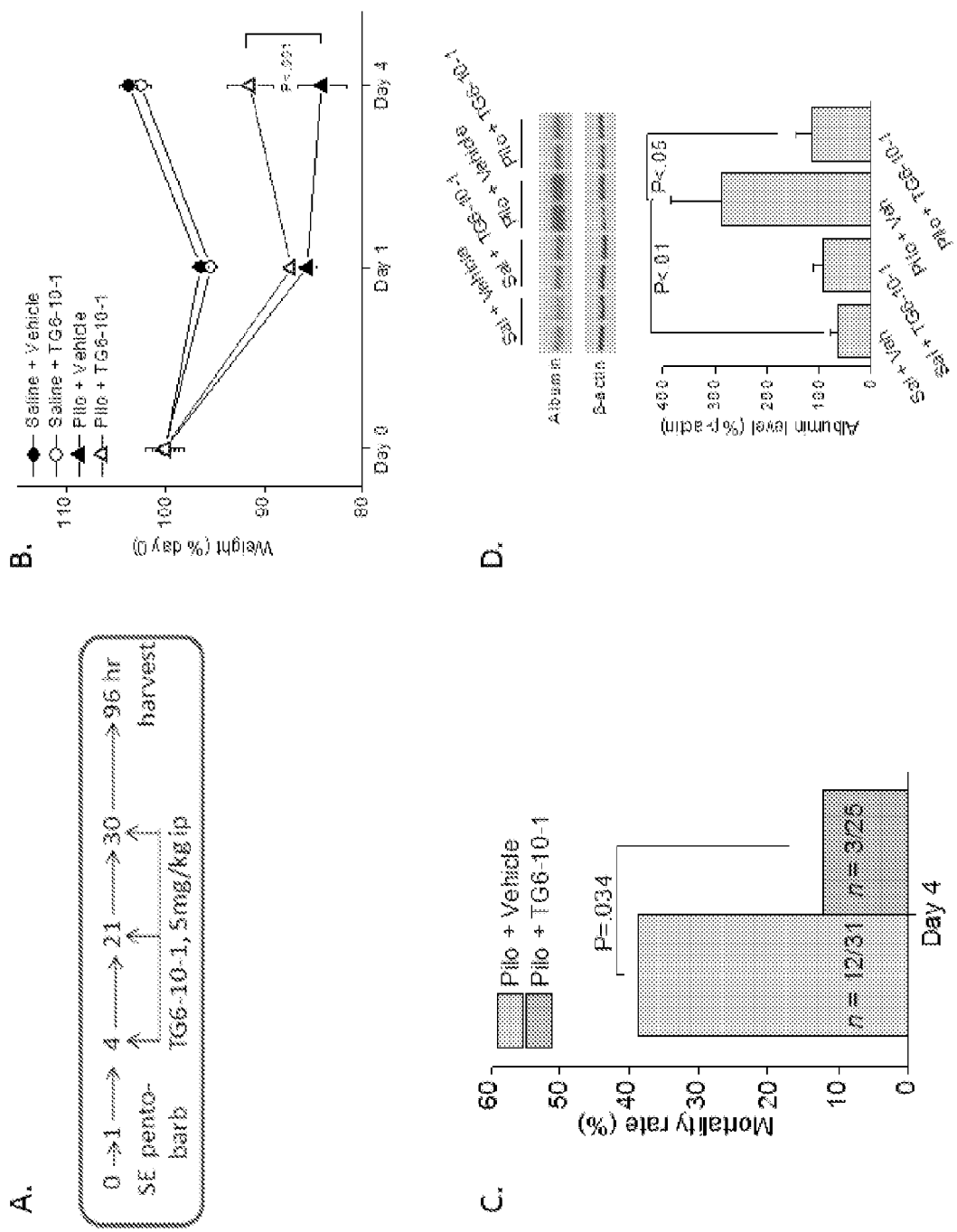
FIG. 8 shows data suggesting EP2 inhibition reduces weight loss and blood-brain barrier (BBB) destruction after pilocarpine-induced status epilepticus. Pilocarpine-induced status epilepticus was allowed to proceed for 60 min, terminated by pentobarbital (25 mg/kg ip). Three doses of compound 1h were administered (5 mg/kg, IP) at 4, 10 and 30 hours (panel A). SE caused substantial weight loss of the animals, which was partially prevented by compound 1h by day 4 (P<0.001; panel B). Animals that received compound 1h gained more weight from day 1 to day 4 compared to animals that received vehicle after status epilepticus. The status epilepticus-induced mortality rate by day 4 was also reduced by compound 1h (panel C, p=0.034). Compound 1h significantly prevented leakage of plasma albumin into the cortex four days after status epilepticus, measured by Western blot analysis (P<0.05, panel D).
Figure 9:
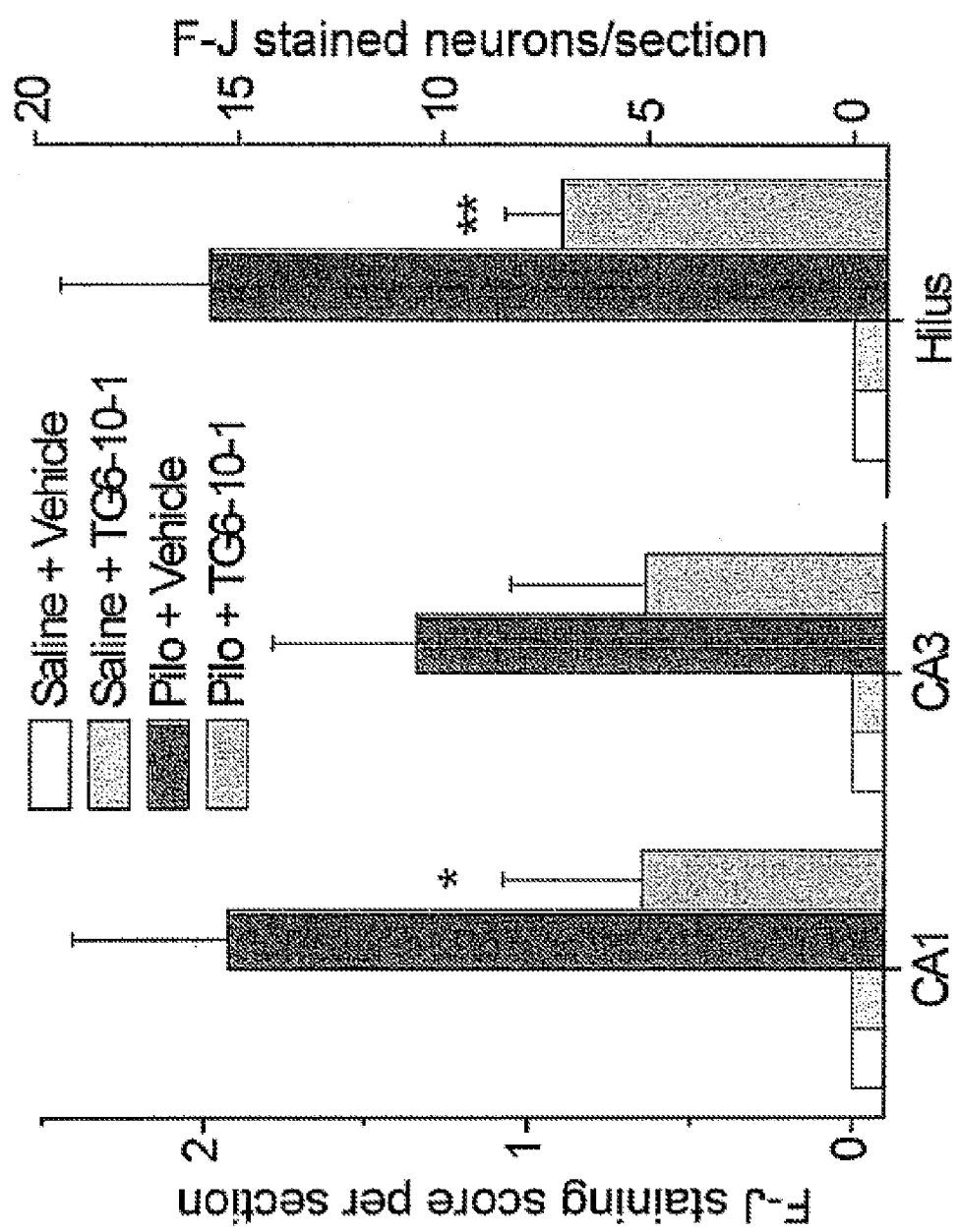
FIG. 9 shows data suggesting neuroprotection in hippocampus by EP2 antagonists administered 3-4 hours after pilocarpine induced status epilepticus. Pilocarpine-induced status epilepticus caused substantial neurodegeneration in hippocampus four days after status epilepticus; whereas no positive staining was detected in animals from the control groups. Administration of compound 1h according to the schedule in FIG. 8A significantly reduced the status epilepticus-induced neurodegeneration by 66% (P<0.05) in CA1, by 52% in CA3, and by 55% (P<0.01) in hilus. These results suggest the EP2 receptor is involved in COX-2-regulated neuroinflammation and neurodegeneration following a seizure.
Figure 10:
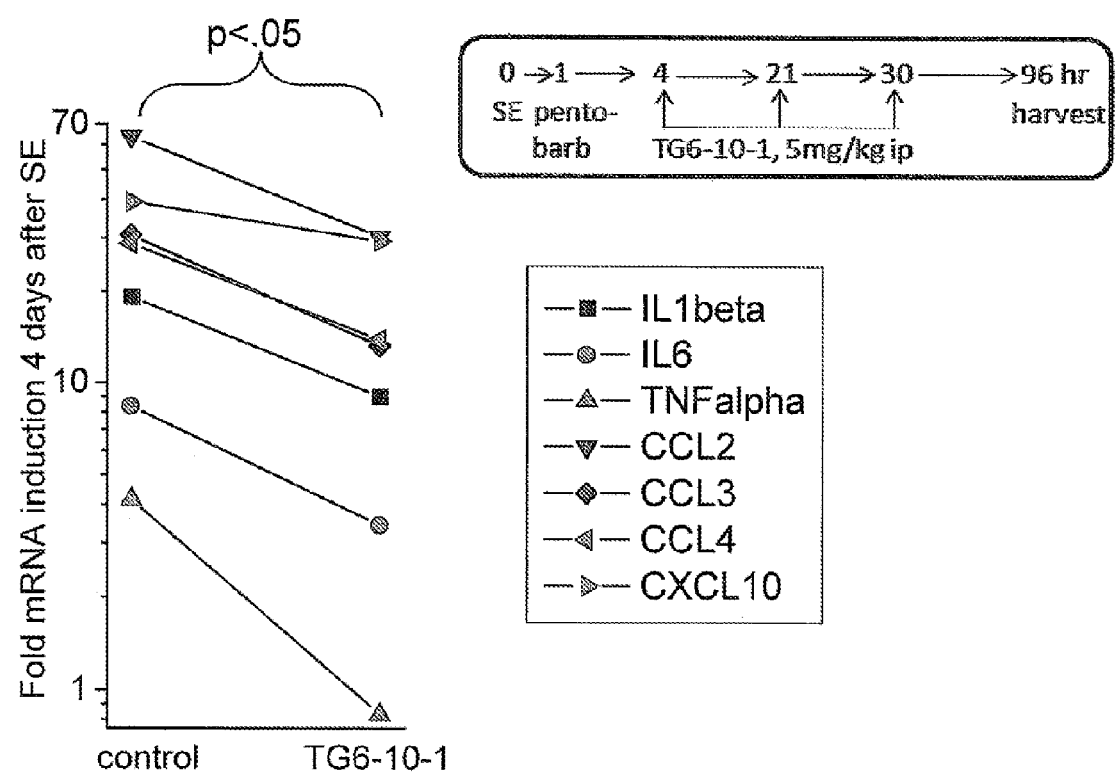
FIG. 10 shows data suggesting blunted cytokine production in hippocampus by EP2 antagonist administered 3-4 hours after pilocarpine induced status epilepticus. The mRNA levels of cytokines—IL-1β, IL-6, TNFα, and chemokines—CCL2, CCL3, CCL4, CXCL10 in hippocampi from mice that received vehicle or compound 1h four days after status epilepticus were measured by quantitative real-time polymerase chain reaction (qRT-PCR). All seven cytokines and chemokines, considered as a group, were substantially induced by status epilepticus and administration of 1h largely blunted the induction by an average of 54% (P<0.05).

Certain compounds were identified as antagonists of the human EP2 receptor through high-throughput screening (HTS) and follow-on medicinal chemistry. These EP2 antagonist compounds are shown to suppress EP2-regulated prostate cancer cell growth and invasion in vitro. In addition, certain compounds also display substantial neuroprotection in an in vitro excitotoxicity model and can quash EP2-regulated microglial activation characterized by upregulation of inflammatory mediators such as inducible nitric oxide synthase (iNOS) and cyclooxygenase-2 (COX-2). Certain of these compounds have low cellular toxicity and represent competitive antagonists of the EP2 prostaglandin receptor.

Prostaglandin Receptor EP2 Antagonists/Inhibitors

In certain embodiments, the disclosure relates to compositions comprising a compound of Formula I,

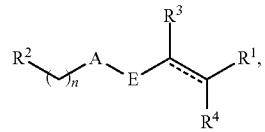

Formula I or pharmaceutically acceptable salt or prodrug thereof, wherein;

----- is a single or double bond;
A is $NR^5$, $CR^6R^7$, O, or S;
E is S, SO, $SO_2$, C=O, C=S, C=N—$OR^8$;
n is 1, 2, 3, or 4;
$R^1$ and $R^2$ are each, the same or different, carbocyclyl, aryl, or heterocyclyl, wherein $R^1$ and $R^2$ are optionally substituted with one or more, the same or different, $R^{10}$;
$R^3$, $R^4$, $R^5$, $R^6$, $R^7$, and $R^8$, are each, the same or different, hydrogen or alkyl, wherein $R^3$, $R^4$, $R^5$, $R^6$, $R^7$, and $R^8$ are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl; aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, $R^1$ is aryl optionally substituted with one or more alkoxy. Typically, the aryl is phenyl. In certain embodiment, $R^2$ is a heterocyclyl optionally substituted with one or more $R^{10}$. Typically, the heterocyclyl is indolyl or benzoimidazolyl.

Examples of Compounds of Formula I Include

N-(2-(2-methyl-1H-indol-1-yl)ethyl)-3-(3,4,5-trimethoxyphenyl)acrylamide,
3-(3,4-dimethoxyphenyl)-N-(2-(2-methyl-1H-indol-1-yl) ethyl)acrylamide,
N-(2-(2-methyl-1H-benzo[d]imidazol-1-yl)ethyl)-3-(3,4,5-trimethoxyphenyl)acrylamide,
3-(3,4-dimethoxyphenyl)-N-(2-(2-methyl-1H-benzo[d]imidazol-1-yl)ethyl)acrylamide, 3-(benzo[d][1,3]dioxol-5-yl)-N-(2-(2-methyl-1H-benzo[d]imidazol-1-yl)ethyl)acrylamide,
N-(2-(1H-benzo[d]imidazol-1-yl)ethyl)-3-(3,4,5-trimethoxyphenyl)acrylamide,
N-(2-(5-fluoro-2-methyl-1H-indol-1-yl)ethyl)-3-(3,4,5-trimethoxyphenyl)acrylamide,
3-(3,4-dimethoxyphenyl)-N-(2-(5-fluoro-2-methyl-1H-indol-1-yl)ethyl)acrylamide,
N-(2-(5-fluoro-2-(trifluoromethyl)-1H-indol-1-yl)ethyl)-3-(3,4,5-trimethoxyphenyl)acrylamide,
3-(3,4-dimethoxyphenyl)-N-(2-(5-fluoro-2-(trifluoromethyl)-1H-indol-1-yl)ethyl)acrylamide,
N-(3-(2-methyl-1H-indol-1-yl)propyl)-3-(3,4,5-trimethoxyphenyl)acrylamide,
N-methyl-N-(2-(2-methyl-1H-indol-1-yl)ethyl)-3-(3,4,5-trimethoxyphenyl)acrylamide,
N-(2-(2-methyl-1H-indol-1-yl)ethyl)-3-(3,4,5-trimethoxyphenyl)propanamide,
3-(4-methoxyphenyl)-N-(2-(2-methyl-1H-indol-1-yl)ethyl)acrylamide,
N-(2-(5-fluoro-2-methyl-1H-indol-1-yl)ethyl)-3-(4-methoxyphenyl)acrylamide,
3-(benzo[d][1,3]dioxol-5-yl)-N-(2-(2-methyl-1H-indol-1-yl)ethyl)acrylamide,
3-(4-ethoxy-3-methoxyphenyl)-N-(2-(2-methyl-1H-indol-1-yl)ethyl)acrylamide,
3-(4-isobutylphenyl)-N-(2-(2-methyl-1H-indol-1-yl)ethyl)acrylamide,
3-(3,4-difluorophenyl)-N-(2-(2-methyl-1H-indol-1-yl)ethyl)acrylamide,
3-(3,4-difluorophenyl)-N-(2-(5-fluoro-2-methyl-1H-indol-1-yl)ethyl)acrylamide,
N-(2-(2-methyl-1H-indol-1-yl)ethyl)-3-(3,4,5-trifluorophenyl)acrylamide,
N-(2-(5-fluoro-2-methyl-1H-indol-1-yl)ethyl)-3-(3,4,5-trifluorophenyl)acrylamide,
3-(3-bromo-4,5-dimethoxyphenyl)-N-(2-(5-fluoro-2-methyl-1H-indol-1-yl)ethyl)acrylamide,
3-(4-chloro-3-methoxyphenyl)-N-(2-(2-methyl-1H-indol-1-yl)ethyl)acrylamide,
3-(4-chloro-3-methoxyphenyl)-N-(2-(5-fluoro-2-methyl-1H-indol-1-yl)ethyl)acrylamide,
3-(5-bromo-2,4-dimethoxyphenyl)-N-(2-(2-methyl-1H-indol-1-yl)ethyl)acrylamide,
N-(2-(2-(trifluoromethyl)-1H-indol-1-yl)ethyl)-3-(3,4,5-trimethoxyphenyl)acrylamide,
3-(3,5-dimethoxyphenyl)-N-(2-(2-methyl-1H-indol-1-yl)ethyl)acrylamide,
3-(4-fluoro-3,5-dimethylphenyl)-N-(2-(2-(trifluoromethyl)-1H-indol-1-yl)ethyl)acrylamide, and
3-(4-fluoro-3,5-dimethylphenyl)-N-(2-(2-methyl-1H-indol-1-yl)ethyl)acrylamide or salts thereof.

In certain embodiments, compounds of Formula I have Formula IA,

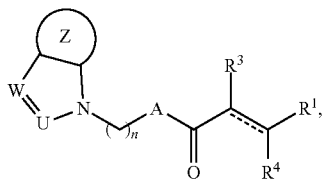

Formula IA or pharmaceutically acceptable salt or prodrug thereof, wherein:
----- is a single or double bond;
A is $NR^5$, $CR^6R^7$, O, or S;
U is $CX^5$ or N;
W is $CX^6$ or N;
Z is a 5 to 7 membered carbocyclyl, aryl, or heterocyclyl;
n is 1, 2, 3, or 4;
$R^1$ is carbocyclyl, aryl, or heterocyclyl, wherein $R^1$ is optionally substituted with one or more, the same or different, $R^{10}$;
$R^3$, $R^4$, $R^5$, $R^6$, and $R^7$, are each, the same or different, hydrogen or alkyl, wherein $R^3$, $R^4$, $R^5$, $R^6$, and $R^7$, are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, W is N and U is CX⁵ and X⁵ is alkyl.

In certain embodiments, compounds of Formula I have Formula IB,

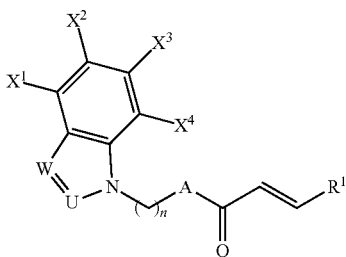

Formula IB or pharmaceutically acceptable salt or prodrug thereof, wherein:

A is NR⁵, CR⁶R⁷, O, or S;
U is CX⁵ or N;
W is CX⁶ or N;
n is 1, 2, 3, or 4;
R¹ is carbocyclyl, aryl, or heterocyclyl, wherein R¹ is optionally substituted with one or more, the same or different, R¹⁰;
R⁵, R⁶, and R⁷, are each, the same or different, hydrogen or alkyl, wherein R⁵, R⁶, and R⁷ are optionally substituted with one or more, the same or different, R¹⁰;
R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;
R¹¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹¹ is optionally substituted with one or more, the same or different, R¹²;
R¹² is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹² is optionally substituted with one or more, the same or different, R¹³;
R¹³ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
X¹, X², X³, and X⁴ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹, X², X³, and X⁴ are optionally substituted with one or more, the same or different, X¹⁰;
X⁵ and X⁶ are each, the same or different, hydrogen or alkyl, wherein X⁵ and X⁶ are optionally substituted with one or more, the same or different, X¹⁰;
X¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹⁰ is optionally substituted with one or more, the same or different, X¹¹; and
X¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamine, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula I have Formula IC,

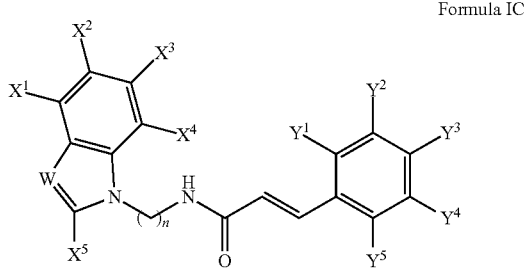

Formula IC or pharmaceutically acceptable salt or prodrug thereof, wherein:

W is CX⁶ or N;
n is 1, 2, 3, or 4;
X¹, X², X³, and X⁴ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹, X², X³, and X⁴ are optionally substituted with one or more, the same or different, X¹⁰;
X⁵ and X⁶ are each, the same or different, hydrogen or alkyl, wherein X⁵ and X⁶ are optionally substituted with one or more, the same or different, X¹⁰;
X¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹⁰ is optionally substituted with one or more, the same or different, X¹¹;
X¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

With regard to any of the embodiments of Formula I, $Y^2$, $Y^3$, and $Y^4$ may be alkoxy or halogen, $X^2$ may be halogen, $X^5$ may be alkyl or alkyl substituted with one or more halogen, and $X^6$ may be CH. In certain embodiments, $Y^3$ and $Y^4$ form a heterocyclic ring. In certain embodiments, n is 2, or 3.

In certain embodiments, $Y^2$ and $Y^4$ may be alkoxy or alkyl.

In certain embodiments, $Y^3$ is hydrogen or halogen.

In certain embodiments, compounds of Formula I have Formula ID,

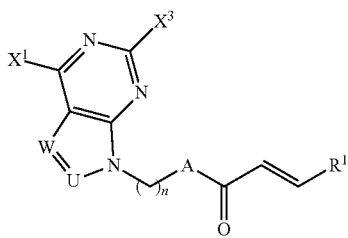

Formula ID or pharmaceutically acceptable salt or prodrug thereof, wherein:

A is NR$^5$, CR$^6$R$^7$, O, or S;
U is CX$^5$ or N;
W is CX$^6$ or N;
n is 1, 2, 3, or 4;
R$^1$ is carbocyclyl, aryl, or heterocyclyl, wherein R$^1$ is optionally substituted with one or more, the same or different, R$^{10}$;
R$^5$, R$^6$, and R$^7$, are each, the same or different, hydrogen or alkyl, wherein R$^5$, R$^6$, and R$^7$ are optionally substituted with one or more, the same or different, R$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$;

R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$ and $X^3$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$ and $X^3$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is NH, n is 2, U is CX$^5$ and W is CX$^6$.

In certain embodiments, compounds of Formula I have Formula IE,

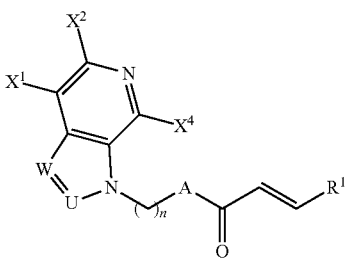

Formula IE or pharmaceutically acceptable salt or prodrug thereof, wherein:

A is $NR^5$, $CR^6R^7$, O, or S;
U is $CX^5$ or N;
W is $CX^6$ or N;
n is 1, 2, 3, or 4;
$R^1$ is carbocyclyl, aryl, or heterocyclyl, wherein $R^1$ is optionally substituted with one or more, the same or different, $R^{10}$;
$R^5$; $R^6$, and $R^7$, are each, the same or different, hydrogen or alkyl, wherein $R^5$, $R^6$, and $R^7$ are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$X^1$, $X^2$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is NH, n is 2, U is $CX^5$ and W is $CX^6$.

In certain embodiments, compounds of Formula I have Formula IF,

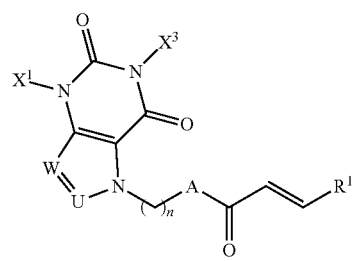

Formula IF or pharmaceutically acceptable salt or prodrug thereof, wherein:

A is $NR^5$, $CR^6R^7$, O, or S;
U is $CX^5$ or N;
W is $CX^6$ or N;
n is 1, 2, 3, or 4;
$R^1$ is carbocyclyl, aryl, or heterocyclyl, wherein $R^1$ is optionally substituted with one or more, the same or different, $R^{10}$;
$R^5$, $R^6$, and $R^7$, are each, the same or different, hydrogen or alkyl, wherein $R^5$, $R^6$, and $R^7$ are optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$ and $X^3$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$ and $X^3$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is NH, n is 2, U is $CX^5$ and W is $CX^6$.

In certain embodiments, compounds of Formula I have Formula IG,

Formula IG

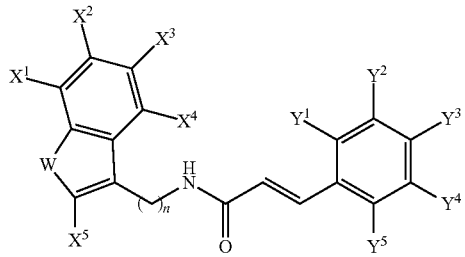

or pharmaceutically acceptable salt or prodrug thereof, wherein:

W is $NX^6$ or O;

n is 1, 2, 3, or 4;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, W is NH.

In certain embodiments, the compounds are selected from:

N-(2-(2-methyl-1H-indol-3-yl)ethyl)-3-(3,4,5-trimethoxyphenyl)acrylamide, 3-(3,4-dimethoxyphenyl)-N-(2-(2-methyl-1H-indol-3-yl)ethyl)acrylamide, N-(2-(5,7-difluoro-2-methyl-1H-indol-3-yl)ethyl)-3-(3,4,5-trimethoxyphenyl)acrylamide, and 4-acetamido-N-(2-(2-methyl-1H-indol-3-yl)ethyl)benzamide, or salts thereof.

In certain embodiments, compounds have Formula II,

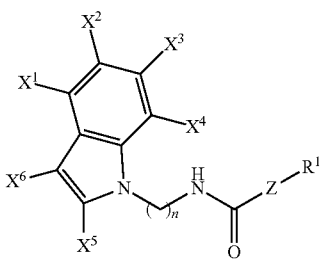

Formula II or pharmaceutically acceptable salt or prodrug thereof, wherein:

Z is —CH$_2$CH$_2$—, or a direct bond;

n is 1, 2, 3, or 4;

R$^1$ is a carbocyclyl, aryl, or heterocyclyl, wherein R$^1$ is optionally substituted with one or more, the same or different, R$^{10}$;

X$^1$, X$^2$, X$^3$, and X$^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^1$, X$^2$, X$^3$, and X$^4$ are optionally substituted with one or more, the same or different; X$^{10}$;

X$^5$ and X$^6$ are each, the same or different, hydrogen or alkyl, wherein X$^5$ and X$^6$ are optionally substituted with one or more, the same or different, X$^{10}$;

X$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^{10}$ is optionally substituted with one or more, the same or different, X$^{11}$;

X$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiment, n is 2. In certain embodiments, Z is a direct bond.

In certain embodiments, R$^1$ is aryl or phenyl.

In certain embodiments, R$^1$ is quinolinyl.

In certain embodiments, compounds of Formula II have Formula IIA,

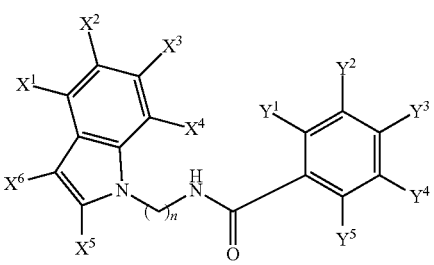

Formula IIA or pharmaceutically acceptable salt or prodrug thereof, wherein:

n is 1, 2, 3, or 4;

X$^1$, X$^2$, X$^3$, and X$^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^1$, X$^2$, X$^3$, and X$^4$ are optionally substituted with one or more, the same or different, X$^{10}$;

X$^5$ and X$^6$ are each, the same or different, hydrogen or alkyl, wherein X$^5$ and X$^6$ are optionally substituted with one or more, the same or different, X$^{10}$;

X$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^{10}$ is optionally substituted with one or more, the same or different, X$^{11}$;

X$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl Y$^1$, Y$^2$, Y$^3$, Y$^4$, and Y$^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein Y$^1$, Y$^2$, Y$^3$, Y$^4$, and Y$^5$ are optionally substituted with one or more, the same or different, Y$^{10}$;

Y$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamine, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, $Y^2$ is hydrogen and $Y^3$ and $Y^4$ are each selected from hydrogen, hydroxy, amino, alkyl, alkoxy or halogen $Y^3$ and $Y^4$ are optionally substituted with one or more, the same or different, $Y^{10}$.

In certain embodiment, $Y^2$ is halogen.

In certain embodiments, $Y^3$ is an amino or heterocyclyl, wherein $Y^3$ is optionally substituted with one or more, the same or different, $Y^{10}$.

In certain embodiments, the compounds are selected from:
3,4-dimethoxy-N-(2-(2-methyl-1H-indol-1-yl)ethyl)benzamide,
4-acetamido-N-(2-(2-methyl-1H-indol-1-yl)ethyl)benzamide,
3-fluoro-N-(2-(2-methyl-1H-indol-1-yl)ethyl)-4-(piperazin-1-yl)benzamide,
4-(dimethylamino)-N-(2-(2-methyl-1H-indol-1-yl)ethyl) benzamide,
4-amino-N-(2-(2-methyl-1H-indol-1-yl)ethyl)benzamide, and
4-cyano-N-(2-(2-methyl-1H-indol-1-yl)ethyl)benzamide, or salts thereof.

Prostaglandin Receptor EP2 Related Diseases and Conditions

Prostaglandin EP2 receptor related diseases or conditions include neurological disorders, brain injury, neuropathic pain, hypertension, ischemic injury, neuroinflammation after a seizure, endometriosis, cancer, inflammatory bowel disease (colitis), arthritis/rheumatoid arthritis, skin inflammation, vascular inflammation, Alzheimer's disease (AD), Parkinson's disease (PD), and amyotrophic lateral sclerosis (ALS), kidney disease/transplant rejection, atherosclerosis, ischaemic heart disease, acne vulgaris, asthma, chronic prostatitis, glomerulonephritis, hypersensitivities, inflammatory bowel diseases, pelvic inflammatory disease, sarcoidosis, vasculitis, interstitial cystitis, and other autoimmune diseases.

Neurological disorders, diseases, or conditions contemplated include, brain injury such as brain damage according to cerebral lobe, basal ganglia, cerebellum, brainstem, frontal lobe damage, parietal lobe damage, temporal lobe damage, occipital lobe damage, aphasia, dysarthria, apraxia, agnosia, amnesia, spinal cord disorders, peripheral nervous system disorders, cranial nerve disorders, autonomic nervous system disorders, seizure disorders such as epilepsy, movement disorders such as Parkinson's disease, sleep disorders, headaches (including migraine), lower back and neck pain, neuropathic pain, delirium and dementia such as in Alzheimer's disease, dizziness, vertigo, stupor, coma, stroke (CVA, cerebrovascular attack), multiple sclerosis (MS) and other demyelinating diseases, infections of the brain or spinal cord (including meningitis), prion diseases, and complex regional pain syndrome (CRPS).

Status epilepticus refers to a potentially life-threatening condition in which the brain is in a state of persistent seizure or recurrent seizure typically lasting longer than about 20-30 minutes. It is not intended that time of the seizure be of any specific duration, but typically 30-60 minutes is sufficient to damage neurons and that seizures are unlikely to self-terminate by that time. The mortality rate of status epilepticus is high, especially if treatment is not initiated soon after. Examples of why one may experience such a seizure include because they have epilepsy and have stopped taking anticonvulsant medication, a stroke, hemorrhage, or as a result of intoxicants, adverse reactions to drugs, consumption of alcoholic beverages, fasting, trauma to the brain, brain disorders such as, but not limited to, meningitis, encephalitis, brain tumors, abscess. It is contemplated that in certain embodiments, the subject may be in a convulsive status epileptics for any of the reasons provided herein.

Status epilepticus may be treated with midazolam, valproate, phenobarbital, thiopental pentobarbital, diazepam or other benzodiazepines such as clonazepam, or lorazepam. If these compounds are ineffective one may administer general anesthetics such as propofol or an NMDA antagonist such as ketamine. In certain embodiments, the disclosure contemplates administering compounds disclosed herein after or in combination with being treated with anticonvulsive agents such as those describe above.

COX-2 and prostanoid products have a role in progression of tumors including lung, head and neck, prostate and colon, ovary and breast, hepatocellular carcinoma. Taking COX-2 inhibitor drugs regularly may reduce the rates of certain cancers and cancer related deaths. Upregulation of COX-2 in tumor tissues has been reported to be accompanied by high levels of $PGE_2$. Moreover, EP2 activation by PGE can promote cancer cell growth and invasion by activating iNOS/guanylate cyclase (GC) and mitogen-activated protein kinase (MAPK)-ERK1/2 via PKA-mediated epidermal growth factor (EGF) receptor activation. $PGE_2$/EP2 signaling in mammary epithelial cells triggers hyperplasia of mammary glands and EP2 receptor is an important element for PGE2 regulated vascular endothelial growth factor (VEGF) induction in mouse mammary tumor cells. EP2 signaling directly regulates tumor angiogenesis in endothelium by enhancing endothelial cell motility and cell survival, mediates epidermal hypertrophy and tumor aggression in response to ultraviolet (UV)-irradiation, and induces skin carcinogenesis.

Thus, within certain embodiments, it is contemplated that compounds disclosed herein may be used for the treatment of cancers and tumors of the nervous system including those subjects diagnosed with cancer, including, skin, blood vessel, lung, head and neck, prostate and colon, ovary and breast cancer and hepatocellular carcinoma.

Within certain embodiments, it is contemplated that compounds disclosed herein may be used for the treatment of inflammation generally and autoimmune diseases, such as, but not limited to, encephalomyelitis, leukoencephalitis, Addison's disease, agammaglobulinemia, alopecia areata, amyotrophic lateral sclerosis; ankylosing spondylitis, anti-GBM/TBM nephritis, antiphospholipid syndrome, antisynthetase syndrome, atopic allergy, atopic dermatitis, aplastic anemia, cardiomyopathy, enteropathy, hemolytic anemia, hepatitis, inner ear disease, lymphoproliferative syndrome, peripheral neuropathy, pancreatitis, polyendocrine syndrome, progesterone dermatitis, thrombocytopenic purpura, urticaria, uveitis, Balo disease/Balo, concentric sclerosis, Bechets syndrome, Berger's disease, Bickerstaff's encephalitis, Blau syndrome, Bullous pemphigoid, Castleman's disease, celiac disease, inflammatory demyelinating polyneuropathy, multifocal osteomyelitis, Churg-Strauss syndrome, cicatricial pemphigoid, Cogan syndrome, cold agglutinin disease, complement component 2 deficiency, cranial arteritis
CREST syndrome, Crohns Disease, Cushing's Syndrome, cutaneous leukocytoclastic angiitis, Dego's disease, Dercum's disease Suspected, dermatitis herpetiformis, dermatomyositis, diabetes mellitus type 1, diffuse cutaneous systemic sclerosis, Dressler's syndrome, Discoid lupus, erythematosus, eczema, enthesitis-related arthritis, eosinophilic fasciitis, eosinophilic, gastroenteritis, epidermolysis bullosa acquisita, erythema nodosum, cryoglobulinemia, Evan's syndrome, fibrodysplasia ossificans progressive, fibrosing aveolitis, gastritis, gastrointestinal pemphigoid, giant cell arteritis, glomerulonephritis, Goodpasture's syndrome, Graves' disease, Guillain-Barré syndrome (GBS), Hashimoto's encephalitis, Hashimoto's thyroiditis, haemolytic anaemia, Henoch-Schonlein purpura, herpes gestationis, hypogammaglobulinemia, demyelinating diseases, pulmonary fibrosis, thrombocytopenic purpura, nephropathy, inclusion body myositis, demyelinating polyneuopathy, interstitial cystitis, Kawasaki's Disease, Lambert-Eaton myasthenic syndrome, leukocytoclastic vasculitis, lichen planus, lichen sclerosus, linear IgA disease (LAD), lupoid hepatitis, lupus erythematosus, Majeed syndrome, Meniere's disease, microscopic polyangiitis, Miller-Fisher syndrome, mixed connective tissue disease, morphea, Mucha-Habermann disease, multiple sclerosis, myasthenia gravis, myositis, meuromyelitis optica, neuromyotonia, occular cicatricial pemphigoid, psoclonus myoclonus syndrome, ord thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonnage-Turner syndrome, Pars planitis, pemphigus pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis Accepted, psoriatic arthritis, pyoderma gangrenosum, pure red cell aplasia, Rasmussen's encephalitis, Raynaud phenomenon, relapsing polychondritis, Reiter's syndrome, Restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondyloarthropathy, Still's disease, stiff person syndrome, subacute bacterial endocarditis (SBE), Susac's syndrome, Sweet's syndrome, sydenham chorea, sympathetic ophthalmia, Takayasu's arteritis, temporal arteritis, Tolosa-Hunt syndrome, transverse myelitis, ulcerative colitis, undifferentiated connective tissue disease, undifferentiated spondyloarthropathy, vasculitis, vitiligo, and Wegener's granulomatosis.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the inhibitors can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, am itriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenyloin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

TERMS

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C═O)alkyl).

"Alkyloxycarbonyl" refers to an alkyl as defined above attached through a carboxy bridge (i.e., —(C═O)Oalkyl.

"Alkylcarbamoyl" refers to an alkyl as defined above attached through a carbonyl bridge (i.e., —(C═O)NHalkyl).

"Alkanoyl" refers to an alkyl as defined above attached through a carbonyl bridge (i.e., —(C═O)alkyl).

"Alkylsulfonyl" refers to an alkyl as defined above attached through a sulfonyl bridge (i.e., —S(═O)$_2$alkyl) such as mesyl and the like, and "Arylsulfonyl" refers to an aryl attached through a sulfonyl bridge (i.e., —S(═O)$_2$aryl).

"Alkylsulfonamide" refers to an alkyl as defined above attached through a sulfamoyl bridge (i.e., —S(═O)$_2$NHalkyl), and an "Arylsulfonamide" refers to an alkyl attached through a sulfamoyl bridge (i.e., (i.e., —S(═O)$_2$NHaryl).

"Alkylsulfinyl" refers to an alkyl as defined attached through a sulfinyl bridge (i.e. —S(═O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(═O)R_b$, —$NR_aC(═O)NR_aNR_b$, —$NR_aC(═O)OR_b$, —$NR_aSO_2R_b$, —$C(═O)R_a$, —$C(═O)OR_a$, —$C(═O)NR_aR_b$, —$OC(═O)NR_aR_b$, —$OR_a$, —$SR_a$, —$SOR_a$, —$S(═O)_2R_a$, —$OS(═O)_2R_a$ and —$S(═O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

EXPERIMENTAL

Synthesis of Compounds

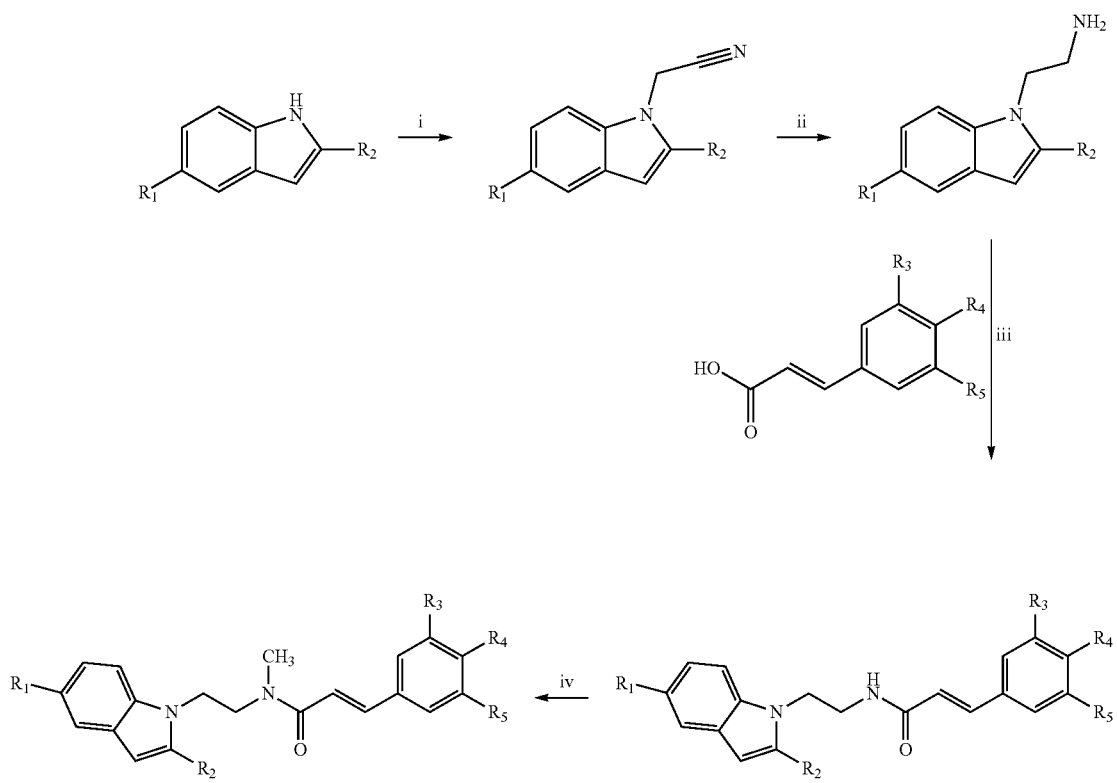

Structure-activity relationship (SAR) analysis based on modifying the structure of compounds A1 and A2 has been conducted to identify potent and selective probe candidates. The synthetic route to the analogs and the resyntheses of A1 (TG4-155) and A2 (TG4-166) are shown above. Typically an indole or substituted indole derivative was treated with 2-bromoacetonitrile in the presence of sodium hydride base. The resulting nitrile intermediates were reduced to amine using lithium aluminium hydride. These amines were coupled either to 3-aryl substituted acrylic acids in the presence of 1-ethyl-3-(3-dimethylaminopropyl) carbodiimide hydrochlroide (EDCI), dimethylaminopyridine (DMAP) in dichloromethane or coupled to 3-aryl substituted acrylyl chlorides in the presence of bases such triethylamine and potassium or sodium carbonates to furnish final products in good to excellent yields. N-Alkylated analogs such as TG6-78 were synthesized by treating the final products with sodium hydride and alkyl halides.

TG4-211-1
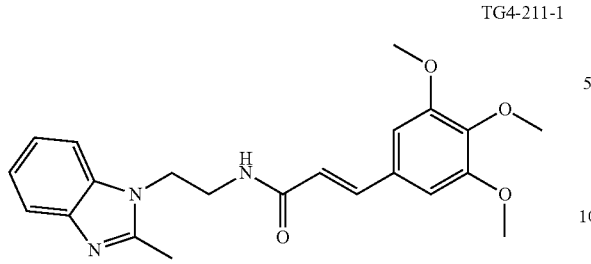
TG6-10-1
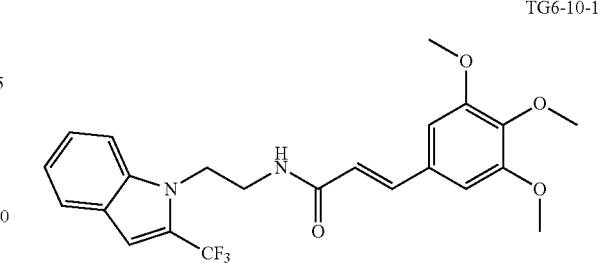
TG4-211-2
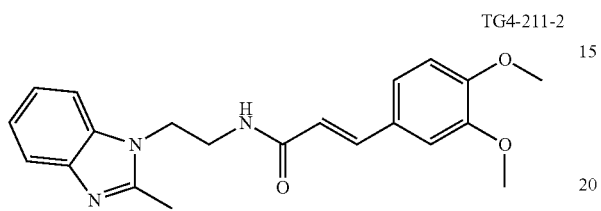
TG6-10-2
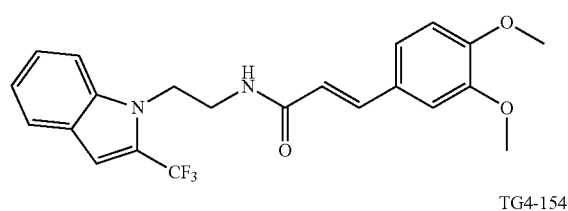
TG4-215-2
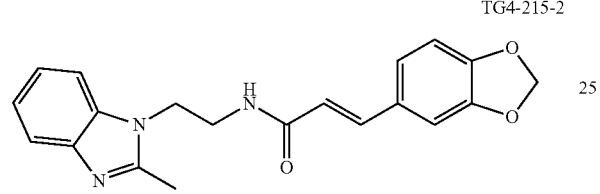
TG4-154
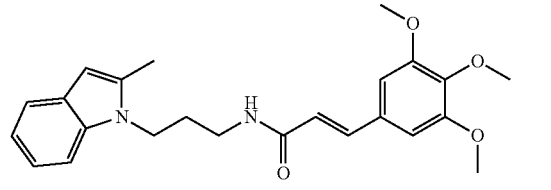
TG4-161
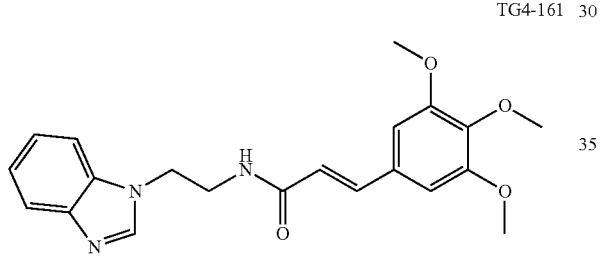
TG6-78
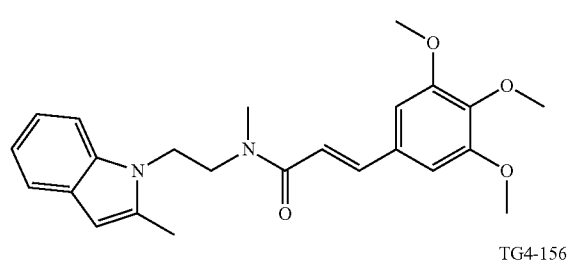
TG6-109-1
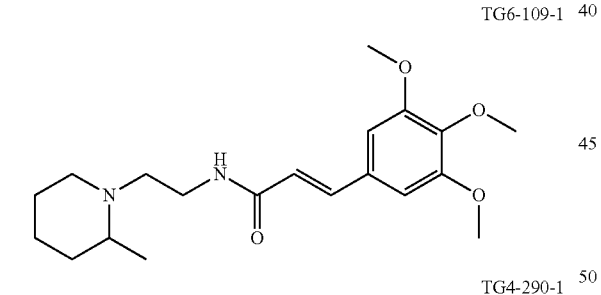
TG4-156
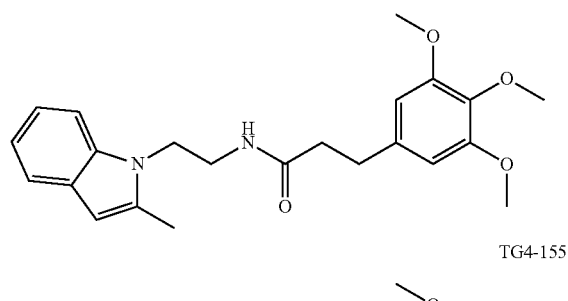
TG4-290-1
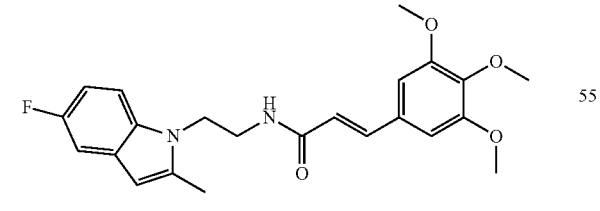
TG4-155
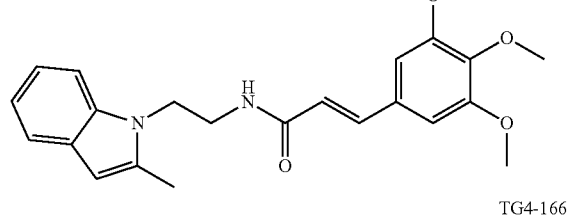
TG4-290-2
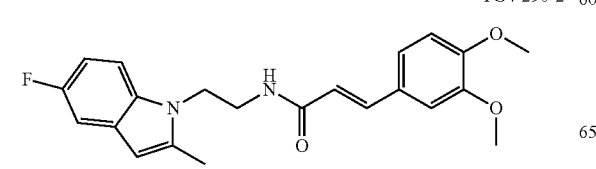
TG4-166
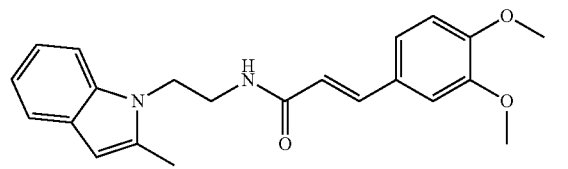

TG6-94-1
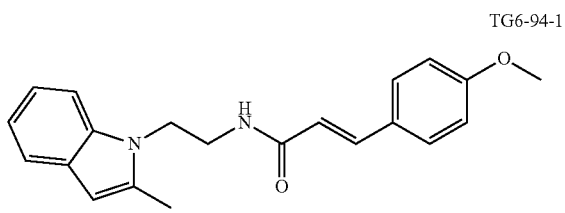

TG6-97-1

TG4-215-1

TG4-292-2

TG6-109-2

TG6-94-2
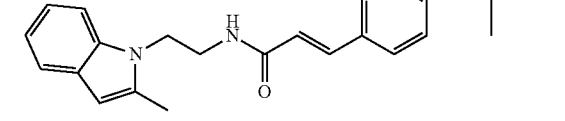

TG6-97-2

TG6-94-3

TG6-97-3
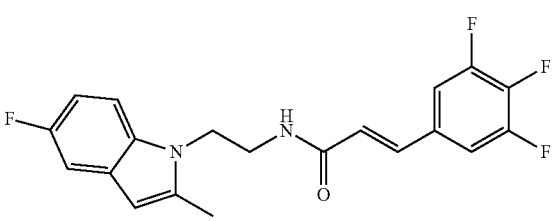

TG4-292-1
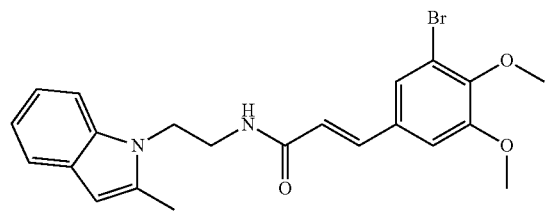

TG4-294-1
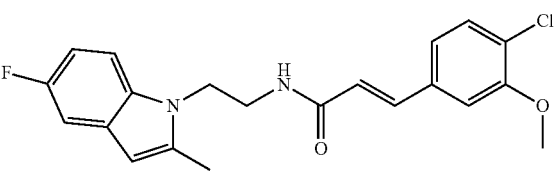

TG4-294-2
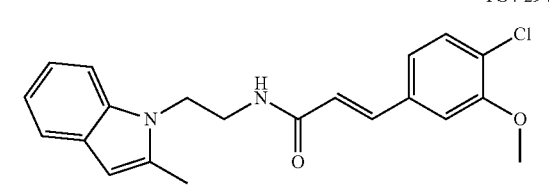

TG6-110
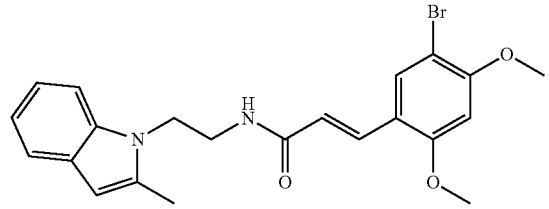

TG4-155 was synthesized as shown. A solution of (E)-3-(3,4,5-trimethoxyphenyl) acrylic acid [220 mg, 0.92 mmol, 1.05 equivalent (eq.)] and dimethylaminopyridine (DMAP) (10 mg) in dichloromethane (6 mL) was added to a solution of 2-(2-methyl-1H-indol-1-yl)ethanamine (152 mg, 0.87 mmol, 1 eq.) in dichloromethane (2 mL), followed by 1-ethyl-3-(3-dimethylaminopropyl) carbodiimide hydrochloride (EDCI) (190 mg, 1 mmol, 1.13 eq.) at room temperature. The resulting solution was stirred for 3 h. At the conclusion of the reaction (monitored by TLC), water (25 mL) was added to quench the reaction. The organics were separated from aqueous phase by extraction with ethyl acetate (3×20 mL). Combined organics were washed with 1% HCl (10 mL), saturated NaHCO$_3$ solution (10 mL), water (10 mL), and brine solution (10 mL). Organics were dried and concentrated to dryness. The resulting crude product was recrystallized with hexane-ethyl acetate mixture to furnish pure compound product TG4-155 (300 mg, 85% yield). Proton NMR spectra were recorded in solvent deuteriochloroform (CDCl$_3$) on a Varian Inova-400 (400 MHz), unless otherwise mentioned.

TG4-155: $^1$H NMR. δ 7.51 (d, J=6.8 Hz, 1H), 7.48 (d, J=15.6 Hz, 1H), 7.29 (d, J=8 Hz, 1H), 7.10 (m, 2H), 6.66 (s, 2H), 6.24 (s, 1H), 6.14 (d, J=15.6 Hz, 1H), 5.6 (t, J=6 Hz, 2H), 4.3 (t, J=6 Hz, 2H), 3.84 (s, 9H), 3.71 (q, J=6 Hz, 2H), 2.39 (s, 3H). Anal. Calcd for C23H26N2O4: C, 70.03; H, 6.64; N, 7.10. Found: C, 69.61; H, 6.61; N, 7.04.

TG4-166: $^1$H NMR. δ 7.52 (d, J=15.6 Hz, 1H), 7.49 (d, J=8 Hz, 1H), 7.26 (d, J=8 Hz, 1H), 7.05 (m, 3H), 6.92 (d, J=2 Hz, 1H), 6.77 (d, J=8.4 Hz, 1H), 6.21 (s, 1H), 6.11 (d, J=15.2 Hz, 1H), 5.89 (t. J=6 Hz, 1H), 4.22 (t, J=6 Hz, 2H), 3.84 (s, 3H), 3.81 (s, 3H), 3.58 (q, J=6 Hz, 2H), 2.36 (s, 3H). Anal. Calcd for C22H24N2O3: C, 72.50; H, 6.64; N, 7.69. Found: C, 72.54; H, 6.70; N, 7.66.

TG4-211-1: $^1$H NMR. δ 7.64 (m, 1H), 7.53 (d, J=15.6 Hz, 1H), 7.3 (m, 1H), 7.20 (m, 2H), 6.6 (s, 2H), 6.20 (d, J=15.6 Hz, 1H), 6.06 (m, 1H), 4.36 (t, J=6 Hz, 2H), 3.84 (s, 9H), 3.75 (q, J=5.6 Hz, 2H), 2.5 (s, 3H). HRMS Calcd for C22H26N3O4 (M+H): 396.19178. Found: 396.19136.

TG4-211-2: $^1$H NMR. δ 7.64 (m, 1H), 7.57 (d, J=15.6 Hz, 1H), 7.31 (m, 1H), 7.19 (m, 2H), 7.04 (dd, J=8.4, 2 Hz, 1H), 6.95 (d, J=2 Hz, 1H), 6.82 (d, J=8.4 Hz, 1H), 6.17 (d, J=15.6 Hz, 1H), 6.08 (s, 1H), 4.35 (t, J=6 Hz, 2H), 3.83 (s, 3H), 3.85 (s, 3H), 3.73 (q, J=6 Hz, 2H), 2.49 (s, 3H). Anal. Calcd for C21H23N3O4: C, 69.02; H, 6.34; N, 11.50. Found: C, 68.77; H, 6.40; N, 11.32.

TG4-215-2: $^1$H NMR. δ 7.56 (m, 1H), 7.45 (d, J=15.6 Hz, 1H), 7.29 (m, 1H), 7.16 (m, 2H), 6.90 (s, 1H), 6.89 (s, 1H), 6.72 (dd, J=8.4, 2 Hz, 1H), 6.1 (d, J=15.6 Hz, 1H), 5.92 (s, 2H), 4.28 (t, J=5.6 Hz, 2H), 3.61 2.45 (s, 3H). HRMS Calcd for C20H20N3O3 (M+H): 350.14992. Found: 350.14960.

TG4-161: $^1$H NMR. δ 7.57 (d, J=7.2 Hz, 1H), 7.56 (s, 1H), 7.51 (d, J=16 Hz, 1H), 7.37 (d, J=8 Hz, 1H), 7.29 (t, J=6 Hz, 1H), 7.20 (t, J=7.6 Hz, 1H), 7.15 (t, J=8 Hz, 1H), 6.59 (s, 2H), 6.33 (d, J=15.6 Hz, 1H), 4.34 (t, J=5.2 Hz, 2H), 3.80 (s, 3H), 3.72 (s. 6H). HRMS Calcd for C21H24N3O4 (M+H): 382.17613. Found: 382.17569.

TG6-109-1: 1 H NMR. δ 7.50 (d, J=15.6 Hz, 1H), 6.89 (s, 1H), 6.70 (s, 2H), 6.34 (d, J=15.6 Hz, 1H), 3.82 (s, 3H), 3.55 (m, 1H), 3.43 (m, 1H), 2.98 (m, 2H), 2.48 (m, 2H), 2.27 (m, 1H), 1.66 (m, 4H), 1.35 (m, 2H), 1.11 (d, J=6.4 Hz, 3H). HRMS Calcd for C20H31N2O4 (M+H): 363.22783. Found: 363.22741.

TG4-290-1: 1H NMR. δ 7.48 (d, J=15.6 Hz, 1H), 7.18 (dd, J=8.8, 4.4 Hz, 1H), 7.13 (dd, J=9.6, 2.4 Hz, 1H), 6.84 (t x d, J=8.8, 2.4 Hz, 1H), 7.63 (s, 2H), 6.20 (s, 1H), 6.15 (d, J=15.6 Hz, 1H), 5.6 (t, J=5.6 Hz, 1H), 4.28 (t, J=6.4 Hz, 1H), 3.84 (s, 9H), 3.67 (q, J=6 Hz, 2H), 2.38 (s, 3H). Anal. Calcd for C23H25FN2O4: C, 66.98; H, 6.11; N, 6.79. Found: C, 66.93; H, 6.03; N, 6.69.

TG4-290-2: $^1$H NMR. δ 7.52 (d, J=15.6 Hz, 1H), 7.18 (dd, J=8.8, 4.4 Hz, 1H), 7.13 (dd, J=9.6, 2.4 Hz, 1H), 7.02 (dd, J=8.2, 1.6 Hz, 1H), 6.94 (dd, J=2 Hz, 1H), 6.83 (m, 2H), 6.17 (s, 1H), 6.12 (d, J=15.6 Hz, 1H), 4.2 (t, J=6 Hz, 2H), 3.87 (s, 3H), 3.85 (s, 3H), 3.63 (q, J=6 Hz, 2H), 2.37 (s, 3H). Anal. Calcd for C22H23FN2O3: C, 69.09; H, 6.06; N, 7.33. Found: C, 68.89; H, 6.01; N, 7.20.

TG6-10-1: 1 H NMR. δ 7.59 (d, J=8 Hz, 1H), 7.54 (d, J=8.4, Hz, 1H), 7.50 (d, J=15.2 Hz, 1H), 7.27 (q, J=7.2 Hz, 1H), 7.1 (t, J=7.2 Hz, 1H), 6.89 (s, 1H), 6.63 (s, 2H), 6.4 (t, J=6 Hz, 1H), 6.25 (d, J=15.2 Hz, 1H), 4.4 (t, J=6.4 Hz, 1H), 3.8 (s, 3H), 3.76 (s, 6H), 3.69 (q, J=6.4 Hz, 2H). Anal. Calcd for C23H23F3N2O4: C, 61.60; H, 5.17; N, 6.25. Found: C, 61.34; H, 5.10; N, 6.16.

TG6-10-2: 1H NMR. δ 7.62 (d, J=8 Hz, 1H), 7.56 (d, J=8.4, Hz, 1H), 7.55 (d, J=15.6 Hz, 1H), 7.29 (t, J=8 Hz, 1H), 7.13 (t, J=7.6 Hz, 1H), 7.0 (dd, J=8.6, 2 Hz, 1H), 6.93 (s, 2H), 6.79 (d, J=8 Hz, 1H), 6.17 (d, J=15.6 Hz, 1H), 6.09 (t, J=5.6 Hz, 1H), 4.4 (t, J=6 Hz, 1H), 3.84 (s, 3H), 3.81 (s, 3H), 3.70 (q, J=6 Hz, 2H). Anal. Calcd for C22H21F3N2O4: C, 63.15; H, 5.06; N, 6.70. Found: C, 63.14; H, 5.94; N, 6.66.

TG4-154: 1H NMR. δ 7.51 (d, J=7.6 Hz, 1H), 7.34 (d, J=15.6 Hz, 1H), 7.27 (d, J=8 Hz, 1H), 7.13 (t, J=7.6 Hz, 1H), 7.05 (t, J=8 Hz, 1H), 6.65 (s, 2H), 6.24 (s, 1H), 6.0 (d, J=15.6 Hz, 1H), 5.23 (s, 1H), 4.18 (t, J=6.8 Hz, 2H), 3.87 (s, 6H), 3.85 (s, 3H), 3.04 (q, J=6 Hz, 2H), 2.42 (s, 3H), 2.03 (q, J=6.8 Hz, 2H). Anal. Calcd for C24H28N2O4: C, 70.57; H, 6.91; N, 6.86. Found: C, 70.37; H, 6.94; N, 6.80.

TG6-78: Proton signals were doubled, due to a quaternary nitrogen atom next to double bond, indicating a mixture of two stereoisomers. LCMS: m/z, 409 (M+H) (95% pure). HRMS Calcd for C24H28N2O4 (M+K): 447.16807. Found 447.16780.

TG4-156: $^1$H NMR. δ 7.48 (d, J=7.6 Hz, 1H), 7.20 (d, J=8 Hz, 1H), 7.10 (t, J=7.6 Hz, 1H), 7.04 (t, J=8 Hz, 1H), 6.34 (s, 2H), 6.20 (s, 1H), 5.67 (t, J=6 Hz, 1H), 4.13 (t. J=6 Hz, 2H), 3.77 (s, 9H), 3.47 (q, J=6 Hz, 2H), 2.80 (t, J=7.6 Hz, 2H), 2.34 (s, 3H), 2.30 (t, J=7.2 Hz, 2H). HRMS Calcd for C23H29N2O4 (M+H): 397.21218. Found: 397.21177.

TG6-94-1: $^1$HNMR (CDCl$_3$+drops of MeOH-d$_4$) δ 7.46 (d, J=15.6 Hz, 1H), 7.44 (d, J=7.2 Hz, 1H), 7.34 (dd, J=6.8, 2 Hz, 2H), 7.24 (d, J=8 Hz, 1H), 7.04 (m, 1H), 7.0 (m, 1H), 6.80 (dd, J=6.8, 2 Hz, 2H), 6.17 (s, 1H), 6.10 (d, J=15.6 Hz, 1H), 4.2 (t, J=6 Hz, 2H), 3.70 (s, 3H), 3.56 (q, J=6 Hz, 2H), 2.3 (s, 3H). HRMS Calcd for C21H22N2O3 (M+K): 373.13129. Found: 373.13093.

TG6-97-1: $^1$H NMR (CDCl$_3$+drops of MeOH-d$_4$) δ 7.52 (d, J=15.6 Hz, 1H), 7.37 (d, J=8.8 Hz, 2H), 7.16 (dd, J=8.8, 4 Hz, 1H), 7.15 (dd, J=10.8, 2.4 Hz, 1H), 6.83 (m, 3H), 6.17 (s, 1H), 6.11 (d, J=15.6 Hz, 1H), 4.23 (t, J=6 Hz, 2H), 3.78 (s, 3H), 3.61 (q, J=6 Hz, 2H), 2.3 (s, 3H). Anal. Calcd for C21H21FN2O2: C, 71.57; H, 6.01; N, 7.95. Found: C, 71.40; H, 6.16; N, 7.88.

Synthesis of 3-fluoro-N-(2-(2-methyl-1H-indol-1-yl) ethyl)-4-(4-methylpiperazin-1-yl)benzamide (TG7-141)

A solution of 3-fluoro-4-(4-methylpiperazin-1-yl)benzoic acid (75 mg, 0.31 mmol, 1 eq.), dimethylaminopyridine (DMAP) (5 mg) in dichloromethane (6 ml) was added to a solution of 2-(2-methyl-1H-indol-1-yl)ethanamine (55 mg, 0.31 mmol, 1 eq.) in dichloromethane (2 ml), followed by 1-ethyl-3-(3-dimethylaminopropyl)carbodiimide.hydrochloride (EDCI) (78 mg, 1.13 eq.) at room temperature. The resulting solution was stirred for 3 h. At the conclusion of the reaction (monitored by thin-layer chromatography), water (25 ml) was added to quench the reaction. The organics were separated from aqueous by extraction with ethyl acetate (3×20 ml). Combined organics were washed with saturated NaHCO$_3$ solution (10 ml), water (10 ml) and brine solution (10 ml). Organics were dried and concentrated to dryness. The resulting crude product was on silica gel chromatography with hexane-ethyl acetate mixture to furnish compound TG7-141 (100 mg, 80% yield). Other compounds were similarly synthesized using appropriate starting materials.

TG7-141: $^1$HNMR. δ 7.49 (dd, J=7.2, 1.2 Hz, 1H), 7.33 (m, 3H), 7.07 (m, 2H), 6.81 (t, J=8.4 Hz, 1H), 6.24 (m, 1H), 6.23 (s, 1H), 4.29 (t, J=5.6 Hz, 2H), 3.70 (q, J=6.4 Hz, 2H), 3.15 (broad t, J=4.4 Hz, 4H), 2.55 (t, J=4.8 Hz, 4H) 2.35 (s, 3H). LCMS calcd for C23H28FN4O (M+H) 395. found: 395.

TG7-142: $^1$H NMR. δ 7.52 (m, 3H), 7.32 (d, J=7.2, Hz, 1H), 7.08 (m, 2H), 6.63 (d, J=8.8 Hz, 2H), 6.23 (s, 1H), 5.9

(NH, 1H), 4.33 (t, J=5.6 Hz, 2H), 3.76 (q, J=6 Hz, 2H), 2.99 (s, 6H), 2.37 (s, 3H). LCMS calcd for C20H23N3O (M+H) 322. found: 322.

TG7-140: $^1$H NMR. δ 7.78 (dd, J=7.2, 1.6 Hz, 2H), 7.62 (dd, J=7.2, 1.6 Hz, 2H), 7.45 (m, 1H), 7.27 (m, 2H), 7.20 (m, 2H), 4.3 (m, 2H), 3.68 (m, 2H), 2.33 (s, 3H). LCMS calcd for C19H20N3O2 (M+H) 322. found: 322.

TG7-112-2: $^1$HNMR. δ 7.51 (dd, J=7.2, 1.6 Hz, 1H), 7.31 (d, J=6.8 Hz, 1H), 7.23 (d, J=2 Hz, 1H), 7.0 (m, 3H), 6.77 (d, J=8.4 Hz, 1H), 6.03 (broad t, NH), 4.34 (t, J=6 Hz, 2H), 3.88 (s, 3H), 3.84 (s, 3H), 3.77 (q, J=6 Hz, 2H), 2.39 (s, 3H). LCMS calcd for C20H23N2O3 (M+H) 339. found: 339.

TG7-117: $^1$H NMR. δ 7.49 (m, 5H), 7.25 (dd, J=7.2 Hz, 1H), 6.98 (m, 2H), 4.23 (t, J=6.4 Hz, 2H), 3.61 (t, J=6.4 Hz, 2H), 2.29 (s, 3H), 2.0 (s, 3H). LCMS calcd for C20H22N3O2 (M+H) 336. found: 336.

TG7-98: $^1$HNMR. δ 7.51 (d, J=7.2 Hz, 1H), 7.50 (d, J=15.6 Hz, 1H), 7.29 (d, J=7.6 Hz, 1H), 7.1 (m, 4H), 6.24 (s, 1H), 6.11 (d, J=15.6 Hz, 1H), 5.57 (NH), 4.3 (t, J=6.4 Hz, 2H), 3.70 (q, J=6.4 Hz, 2H), 2.39 (s, 3H), 2.23 (s, 6H). LCMS calcd for C22H24FN2O (M+H) 351. found: 351.

TG4-215-1: $^1$HNMR. δ 7.50 (d, J=15.6 Hz, 1H), 7.51 (d, J=8 Hz, 1H), 7.29 (d, J=8 Hz, 1H), 7.11 (t, J=7.6 Hz, 1H), 7.06 (d, J=8 Hz, 1H), 6.95 (m, 1H), 6.93 (s, 1H), 6.77 (d, J=8.8 Hz, 1H), 6.24 (s, 1H), 6.02 (d, J=15.6 Hz, 1H), 5.97 (s, 2H), 5.48 (t, J=6 Hz, 1H), 4.29 (t, J=6 Hz, 2H), 3.70 (q, J=6.4 Hz, 2H), 2.39 (s, 3H). HRMS Calcd for C21H21N2O3 (M+H): 349.15467. Found: 349.15454.

TG4-292-2: $^1$H NMR. δ 7.51 (d, J=15.6 Hz, 1H), 7.50 (d, J=7.6 Hz, 1H), 7.27 (d, J=8 Hz, 1H), 7.08 (m, 2H), 6.98 (m, 2H), 6.79 (d, J=8.4 Hz, 1H), 6.23 (s, 1H), 6.1 (d, J=15.2 Hz, 1H), 5.72 (t, J=6.4 Hz, 1H), 4.26 (t, J=6.4 Hz, 2H), 4.08 (q, J=7.2 Hz, 2H), 3.83 (s, 3H), 3.6 (q, J=6.4 Hz, 2H), 2.38 (s, 3H), 1.45 (t, J=7.2 Hz, 3H). HRMS Calcd for C23H26N2O3 (M+K): 417.15750. Found: 417.15684.

TG6-109-2: $^1$HNMR. δ 7.58 (d, J=15.6 Hz, 1H), 7.51 (d, J=7.2 Hz, 1H), 7.35 (d, J=8 Hz, 2H), 7.28 (d, J=8 Hz, 1H), 7.11 (m, 3H), 7.06 (m, 1H), 6.23 (s, 1H), 6.19 (d, J=15.6 Hz, 1H), 5.84 (t, J=6 Hz, 1H), 4.24 (t, J=6 Hz, 2H), 3.6 (q, J=6.4 Hz, 2H), 2.47 (d, J=7.6 Hz, 2H), 2.38 (s, 3H), 0.9 (d, J=6.4 Hz, 6H). Anal. Calcd for C24H28N2O: C, 79.96; H, 7.83; N, 7.77. Found: C, 79.59; H, 7.69; N, 7.67.

TG6-94-2: $^1$H NMR. δ 7.5 (d, J=8.4 Hz, 1H), 7.46 (d, J=15.6 Hz, 1H), 7.22 (m, 2H), 7.10 (m, 4H), 6.2 (s, 1H), 6.09 (d, J=15.6 Hz, 1H), 5.72 (t, J=5.6 Hz, 1H), 4.27 (t, J=6.4 Hz, 2H), 3.65 (q, J=6 Hz, 2H), 2.3 (s, 3H). Anal. Calcd for C20H18F2N2O: C, 70.58; H, 5.33; N, 8.23. Found: C, 70.45; N, 5.39; N, 8.21.

TG6-97-2: $^1$H NMR (CDCl3+drops of MeOH-d4) δ 7.42 (d, J=15.6 Hz, 1H), 7.25 (m, 2H), 7.10 (m, 4H), 6.79 (m, 1H), 6.16 (m, 2H), 6.14 (s, 1H), 4.2 (t, J=6 Hz, 2H), 3.57 (q, J=6 Hz, 2H), 2.33 (s, 3H). Anal. Calcd for C20H17F3N2O: C, 67.03; H, 4.78; N, 7.82. Found: C, 66.81; H, 4.58; N, 7.82.

TG6-94-3: $^1$H NMR. δ 7.49 (d, J=7.2 Hz, 1H), 7.37 (d, J=15.6 Hz, 1H), 7.24 (d, J=8 Hz, 1H), 7.08 (m, 2H), 7.02 (m, 2H), 6.23 (s, 1H), 6.06 (d, J=15.6 Hz, 1H), 5.56 (t, J=4 Hz, 1H), 24 (t, J=6 Hz, 2H), 3.62 (q, J=6 Hz, 2H), 2.37 (s, 3H). HRMS Calcd for C20H17F3N2O (M+K): 397.09246. Found 397.09258.

TG6-97-3: NMR. δ 7.41 (d, J=15.6 Hz, 1H), 7.15 (m, 2H), 7.03 (m, 4H), 6.82 (m, 1H), 6.19 (s, 1H), 6.12 (d, J=15.6 Hz, 1H), 5.78 (t, J=5.6 Hz, 1H), 4.25 (t, J=6 Hz, 2H), 3.63 (q, J=6 Hz, 2H), 2.37 (s, 3H). Anal. Calcd for C20H16F4N2O: C, 63.83; H, 4.29; N, 7.44. Found: C, 63.76; H, 4.13; N, 7.39.

TG4-292-1: $^1$HNMR. δ 7.48 (d, J=7.6 Hz, 1H), 7.40 (d, J=15.6 Hz, 1H), 7.24 (m, 2H), 7.02 (m, 2H), 6.86 (d, J=2 Hz, 1H), 6.22 (s, 1H), 6.13 (d, J=15.6 Hz, 1H), 4.26 (t, J=6.4 Hz, 2H), 3.8 (s, 3H), 3.63 (q, J=6.4 Hz, 2H), 2.3 (s, 3H). HRMS Calcd for C22H23BrN2O3 (M+K): 481.05263. Found: 481.05200.

TG4-294-1: $^1$HNMR. δ 7.50 (d, J=15.6 Hz, 1H), 7.47 (d, J=2.4 Hz, 1H), 7.27 (dd, J=8.6, 1.6 Hz, 1H), 7.17 (dd, J=8.8, 4.4 Hz, 1H), 7.14 (dd, J=9.6, 2.4 Hz, 1H), 6.87 (d, J=8.4 Hz, 1H), 6.83 (t x d, J=8.8, 2.4 Hz, 1H), 6.19 (s, 1H), 6.10 (d, J=16 Hz, 1H), 5.68 (t, J=5.6 Hz, 1H), 4.25 (t, J=6.4 Hz, 2H), 3.89 (s, 3H), 3.64 (q, J=6.4 Hz, 2H), 2.37 (s, 3H). Anal. Calcd for C21H20ClFN2O2: C, 65.20; H, 5.21; N, 7.24. Found: C, 64.94; H, 5.17; N, 7.12.

TG4-294-2: $^1$H NMR. δ 7.46 (m, 2H), 7.42 (d, J=16 Hz, 1H), 7.26 (m, 2H), 7.05 (m, 2H), 6.85 (d, J=8.4 Hz, 1H), 6.43 (t, J=6.4 Hz, 1H), 6.2 (s, 1H), 6.10 (d, J=15.6 Hz, 1H), 4.23 (t, J=6.4 Hz, 2H), 3.86 (s, 3H), 3.61 (q, J=6.4 Hz, 2H), 2.34 (s, 3H). Anal. Calcd for C21H21ClN2O2: C, 68.38; H, 5.74; N, 7.59. Found: C, 67.72; H, 5.76; N, 7.49.

TG6-110: $^1$H NMR. δ 7.75 (d, J=15.6 Hz, 1H), 7.53 (s, 1H), 7.48 (d, J=7.6 Hz, 1H), 7.27 (d, J=8 Hz, 1H), 7.07 (m, 2H), 6.36 (m, 1H), 6.21 (s, 1H), 6.19 (d, J=15.6 Hz, 1H), 4.23 (t, J=6.4 Hz, 2H), 3.87 (s, 3H), 3.79 (s, 3H), 3.60 (q, J=6 Hz, 2H), 2.37 (s, 3H). Anal. Calcd for C22H23BrN2O3: C, 59.60; H, 5.23; N, 6.32. Found: C, 59.47; H, 5.35; N, 6.32.

Characterization of Inhibition by Compounds

Information on the modality of antagonism can be obtained by performing Schild regression analysis characterized by: $\log(dr-1)=\log X_B - \log K_B$. In the equation, dose ratio (dr)=fold shift in $EC_{50}$, $X_B$=[antagonist], $K_B$=equilibrium dissociation constant for the antagonist-receptor complex. A linear regression of $\log(dr-1)$ on $\log X_B$ with a slope of unity characterizes a competitive antagonism and the $K_B$ value indicates the antagonist concentration required for 2-fold rightward shift in the dose-response curve. Thus, a lower $K_B$ value indicates a higher inhibitory potency.

To perform the Schild regression, C6G-EP2 cells were incubated first with vehicle, 0.01, 0.1 or 1 μM of test compound for 5 minutes, then with increasing concentrations of PGE, to activate the EP2 receptor. Hit compounds A1 and A2, and analog compound 1v induced a concentration-dependent rightward shift in the PGE$_2$ dose-response curve. The Schild regression analyses demonstrated that certain test compounds displayed a competitive antagonism in PGE$_2$-induced EP2 activation with $K_B$s: 2.4, 4.6, 1.8 nM and slopes: 1.0, 1.1, 1.2 for A1, A2, 1v, respectively. Analog compound 1v showed an improved potency in EP2 receptor inhibition and only 1.8 nM 1v is required to yield 2-fold rightward shift in the PGE$_2$ dose-response curve in C6G-EP2 cells. The activity cytotoxicity and selectivity for EP2 antagonist are shown in the table below.

| Analog number | Synthesis number | $^a K_B$ (nM) EP2 | $^b CC_{50}$ (μM) | $^c$Therapeutic index | $^d K_B$ (μM) EP4 | $^e$Selective index |
|---|---|---|---|---|---|---|
| A1 | TG4-155 | 2.4 | 172 | 71,700 | 11.4 | 4,730 |
| A2 | TG4-166 | 4.6 | 397 | 86,300 | 2.0 | 435 |

-continued

| Analog number | Synthesis number | $^a K_B$ (nM) EP2 | $^b CC_{50}$ (µM) | $^c$Therapeutic index | $^d K_B$ (µM) EP4 | $^e$Selective index |
|---|---|---|---|---|---|---|
| 1a | TG4-211-1 | 348 | 360 | 1,030 | 13.7 | 39 |
| 1b | TG4-211-2 | 947 | 448 | 473 | 13.3 | 14 |
| 1c | TG4-215-2 | 1,490 | 325 | 219 | 15.3 | 10 |
| 1d | TG4-161 | 2,520 | 311 | 123 | 13.9 | 6 |
| 1e | TG6-109-1 | Inactive | 316 | N/A | 18.9 | N/A |
| 1f | TG4-290-1 | 2.1 | 155 | 73,800 | 5.4 | 2,600 |
| 1g | TG4-290-2 | 22.2 | 264 | 11,900 | 1.7 | 77 |
| 1h | TG6-10-1 | 21.4 | 81 | 3,790 | 13.4 | 626 |
| 1i | TG6-10-2 | 58.8 | 209 | 3,550 | 22.4 | 381 |
| 1j | TG4-154 | 1,860 | 182 | 98 | 5.7 | 3 |
| 1k | TG6-78 | 185 | 278 | 1,500 | 16.6 | 90 |
| 1l | TG4-156 | 214 | 397 | 1,860 | 18.1 | 85 |
| 1m | TG6-94-1 | 16.5 | 3,090 | 187,000 | 8.0 | 484 |
| 1n | TG6-97-1 | 42.4 | 653 | 15,400 | 11.7 | 277 |
| 1o | TG4-215-1 | 18.1 | 146 | 8,070 | 11.4 | 629 |
| 1p | TG4-292-2 | 7.2 | 517 | 71,800 | 1.9 | 268 |
| 1q | TG6-109-2 | 82.4 | 199 | 2,420 | 30.2 | 367 |
| 1r | TG6-94-2 | 3.8 | 89 | 23,400 | 10.6 | 2,800 |
| 1s | TG6-97-2 | 7.0 | 684 | 97,700 | 13.9 | 1,990 |
| 1t | TG6-94-3 | 18.7 | 46 | 2,460 | 17.2 | 921 |
| 1u | TG6-97-3 | 27.8 | 62 | 2,230 | 19.9 | 715 |
| 1v | TG4-292-1 | 1.8 | 696 | 387,000 | 2.2 | 1,200 |
| 1w | TG4-294-2 | 1.9 | 481 | 253,000 | 4.7 | 2,470 |
| 1x | TG4-294-1 | 6.3 | 601 | 95,400 | 3.3 | 525 |
| 1y | TG6-110 | 8.0 | 1,240 | 155,000 | 6.9 | 859 |

$^a K_B$ (nM) value for EP2 receptor from Schild regression analysis.
$^b$Half maximal cytotoxic concentration ($CC_{50}$) in C6G cells after 48 h incubation.
$^c$In vitro therapeutic index determined by $CC_{50}/K_B$ for EP2.
$^d K_B$ (µM) value for EP4 receptor from Schild regression analysis.
$^e$Selectivity index, determined by $K_B$ EP4/$K_B$ EP2.

A lower $K_B$ value indicates a higher inhibitory activity of the compound. A fluorine attached to the methylindol ring (1f and 1g) did not significantly affect the compound potency. If a methoxy was replaced by ethoxy (1p), the inhibition was not significantly affected. However, if the methoxy was replaced by an isobutyl (1o, the inhibition was reduced, compared to 1m. Interestingly, if the methoxy was replaced by fluorine, the potency from difluorophenyl (1r and 1s) is higher than that from trifluorophenyl (1t and 1u). In addition, replacement of methoxy by other halogens such as bromine in 1v, or chlorine in 1w and 1x, also increased the compound potency. Compounds with methylindol or fluoromethylindol ring, ethyl linker, acrylamide, and methoxyphenyl or halogenphenyl displayed robust potency in EP2 inhibition.

DP1 Assay

Both DP1 and EP2 receptors are positively coupled through Gas to cAMP production and conduct very similar physiological and pathological events. Among the eight canonical prostanoid receptors, DP1 has similarities to EP2 at both protein and DNA level. C6G cells that stably expressing human DP1 receptors were seeded into 384-well plates in 30 µL complete medium (4,000 cells per well) and grown overnight. The medium was thoroughly withdrawn and 10 µL HBSS (HyClone) plus 20 µM rolipram were added into the wells to block phosphodiesterase. The cells were incubated at room temperature for 30 min and then treated with vehicle or test compound for 5 min before addition of increasing concentrations of DP1 selective agonist-BW245C for 40 min. The cells were lysed in 10 µL lysis buffer containing the FRET acceptor cAMP-d2 and 1 min later another 10 µL lysis buffer with anti-cAMP-Cryptate was added. After 60-90 min incubation at room temperature, the TR-FRET signal was detected by an Envision 2103 Multilabel Plate Reader (PerkinElmer) with a laser excitation at 337 nm and dual emissions at 665 nm and 590 nm for d2 and Cryptate, respectively. The FRET signal is expressed as $F665/F590 \times 10^4$.

Additional compounds that were tested are provided in the tables below.

| Compound | Structure | EP2 $K_B$ (nM) | DP1 $K_B$ (nM) |
|---|---|---|---|
| TG6-10-1 | 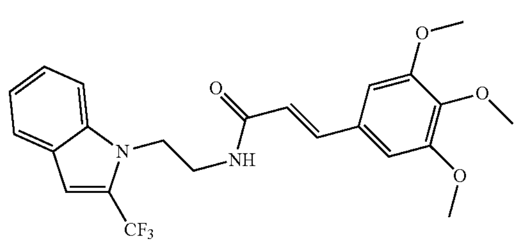 [SMILES: COc1cc(/C=C/C(=O)NCCn2c(C(F)(F)F)cc3ccccc32)cc(OC)c1OC] | 17.8 | 166 |

-continued
| Compound | Structure | EP2 $K_B$ (nM) | DP1 $K_B$ (nM) |
|---|---|---|---|
| TG7-23 | 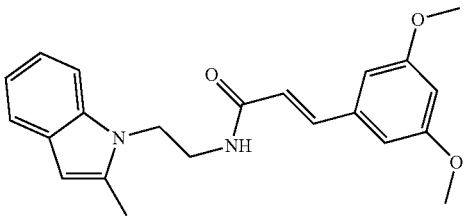 [SMILES: COc1cc(/C=C/C(=O)NCCn2c(C)cc3ccccc32)cc(OC)c1] | 4.7 | Not tested |
| TG7-13 | 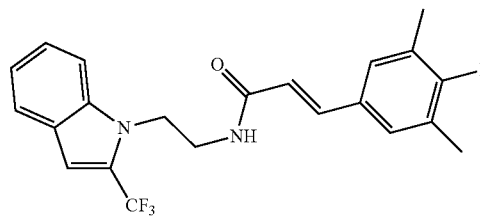 | 288 | Not tested |
| TG7-98 | 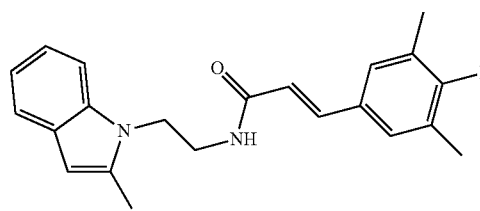 | 4.4 | 745 |
| TG7-122 | 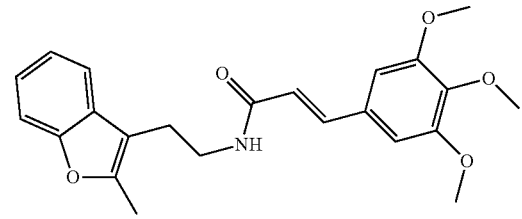 [SMILES: COc1cc(/C=C/C(=O)NCCc2c(C)oc3ccccc23)cc(OC)c1OC] | 217 | Not tested |
| Compound | Structure | EP2 $K_B$ (nM) | DP1 $K_B$ (nM) |
|---|---|---|---|
| TG7-74 | 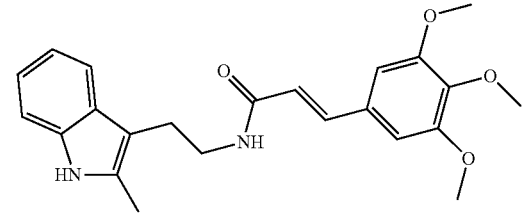 [SMILES: COc1cc(/C=C/C(=O)NCCc2c(C)[nH]c3ccccc23)cc(OC)c1OC] | 2.9 | 112 |
| TG7-76 | 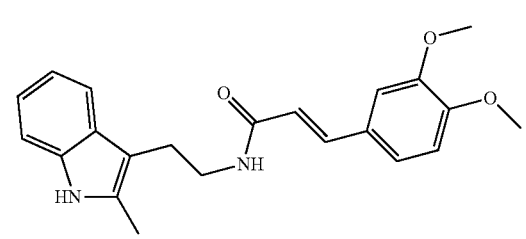 [SMILES: COc1ccc(/C=C/C(=O)NCCc2c(C)[nH]c3ccccc23)cc1OC] | 6.0 | 227 |

-continued

| Compound | Structure | EP2 $K_B$ (nM) | DP1 $K_B$ (nM) |
|---|---|---|---|
| TG7-96 | 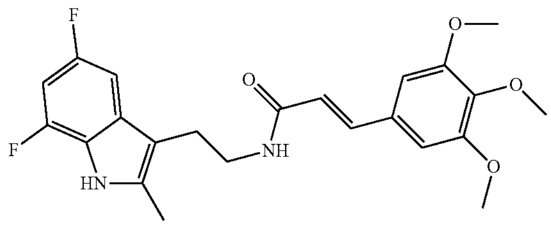 [SMILES: COc1cc(/C=C/C(=O)NCCc2c(C)[nH]c3c(F)cc(F)cc23)cc(OC)c1OC] | 3.5 | 192 |
| TG7-146 | 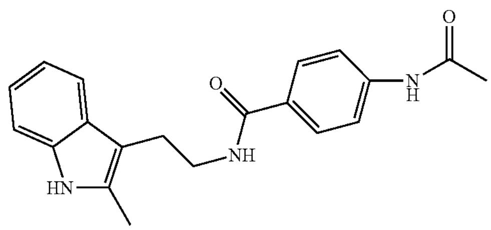 [SMILES: CC(=O)Nc1ccc(C(=O)NCCc2c(C)[nH]c3ccccc23)cc1] | 137.7 | Not tested |

| Compound | Structure | EP2 $K_B$ (nM) | DP1 $K_B$ (nM) |
|---|---|---|---|
| TG7-112-1 | 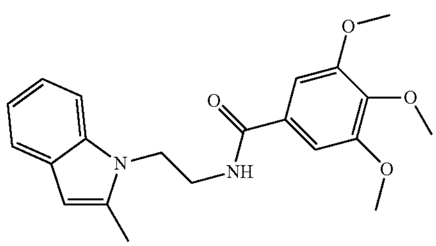 [SMILES: COc1cc(C(=O)NCCn2c(C)cc3ccccc32)cc(OC)c1OC] | >1000 | Not tested |
| TG7-112-2 | 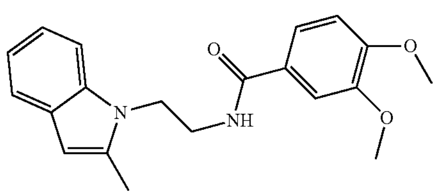 [SMILES: COc1ccc(C(=O)NCCn2c(C)cc3ccccc32)cc1OC] | 22 | 1429 |
| TG7-117 | 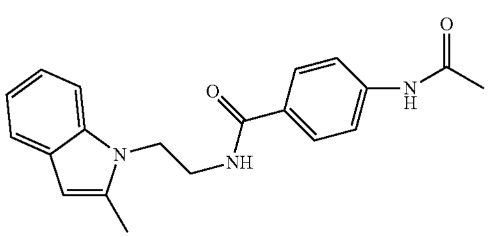 [SMILES: CC(=O)Nc1ccc(C(=O)NCCn2c(C)cc3ccccc32)cc1] | 83 | 5833 |
| TG7-118 | 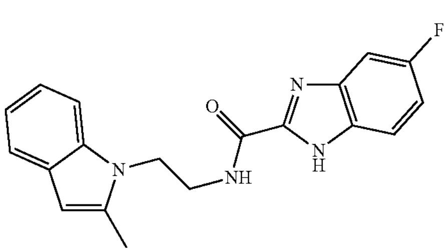 [SMILES: Cc1cc2ccccc2n1CCNC(=O)c1nc2cc(F)ccc2[nH]1] | 128 | Not tested |

-continued

| Compound | Structure | EP2 K$_B$ (nM) | DP1 K$_B$ (nM) |
|---|---|---|---|
| TG7-120 | 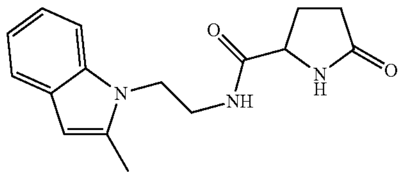 [SMILES: Cc1cc2ccccc2n1CCNC(=O)C1CCC(=O)N1] | >1000 | Not tested |
| TG7-128 | 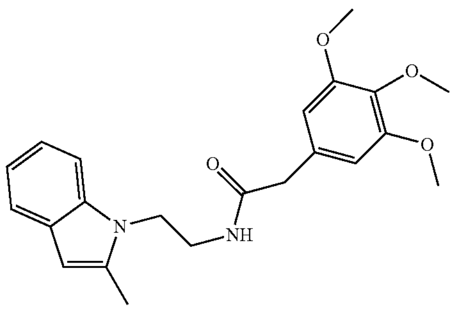 [SMILES: COc1cc(CC(=O)NCCn2c(C)cc3ccccc32)cc(OC)c1OC] | 680 | Not tested |
| TG7-148 | 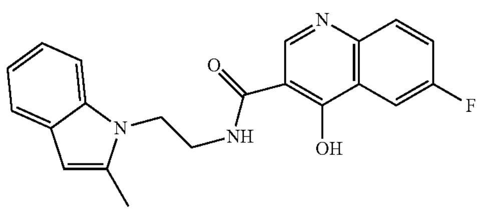 [SMILES: Cc1cc2ccccc2n1CCNC(=O)c1cnc2ccc(F)cc2c1O] | 173.7 | Not tested |
| TG7-131 | 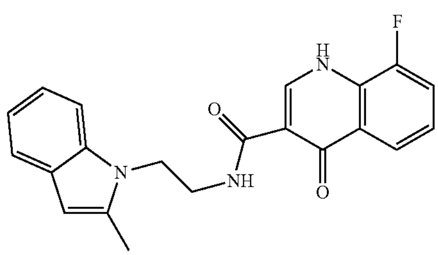 [SMILES: Cc1cc2ccccc2n1CCNC(=O)c1c[nH]c2c(F)cccc2c1=O] | 630 | Not tested |
| TG7-140 | 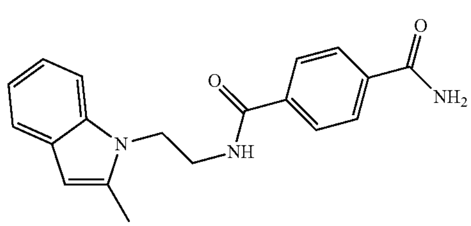 [SMILES: Cc1cc2ccccc2n1CCNC(=O)c1ccc(C(N)=O)cc1] | 150 | Not tested |
| TG7-141 | 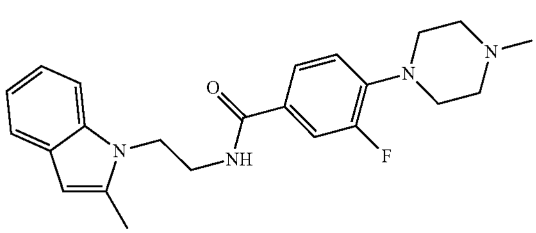 [SMILES: Cc1cc2ccccc2n1CCNC(=O)c1ccc(N2CCN(C)CC2)c(F)c1] | 51.1 | Not tested |

-continued

| Compound | Structure | EP2 $K_B$ (nM) | DP1 $K_B$ (nM) |
|---|---|---|---|
| TG7-142 | 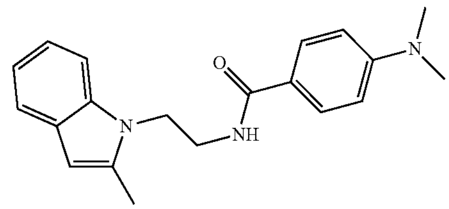 [SMILES: Cc1cc2ccccc2n1CCNC(=O)c1ccc(N(C)C)cc1] | 10.4 | Not tested |
| TG7-143 | 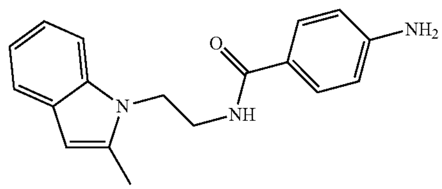 [SMILES: Cc1cc2ccccc2n1CCNC(=O)c1ccc(N)cc1] | 207.3 | Not tested |
| TG7-147 | 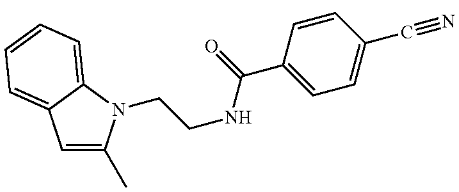 [SMILES: Cc1cc2ccccc2n1CCNC(=O)c1ccc(C#N)cc1] | 139.1 | Not tested |

Certain Compounds can Suppress EP2-Regulated Cancer Cell Proliferation and Invasion $PGE_2$/EP2 signaling has been recognized to play important roles in mediating tumor progression and tumor-associated angiogenesis. Western blot analysis revealed that prostate cancer cell lines DU145, LNCap, and PC3, express a low basal level of COX-2, but substantial amount of EP2. Compound A1 showed a competitive inhibition of butaprost-induced EP2 receptor activation in a concentration dependent manner in PC3 cells. Butaprost-induced EP2 activation promoted PC3 cell growth, measured by MTT cell proliferation assay, in concentration-dependent manner with a maximal response being obtained at 1 μM. Moreover, the butaprost-induced cell growth was attenuated by pretreatment with compound A1 also in a concentration-dependent manner. In addition, EP2 activation by 1 μM butaprost in PC3 cells promoted cell invasion, measured by counting cells that moved across a filter coated with Matrigel. Again, cotreatment with compound A1 (1 μM) also inhibited the EP2 activation-induced cell invasion.

Certain Compounds are Neuroprotective

Excitotoxicity caused by NMDA receptor activation is recognized to induce neuronal apoptosis both in vitro and in vivo in cortical neurons. NMDA receptor activation can, via COX-2, cause prostaglandin production, including $PGE_2$. Activation of the EP2 receptor by $PGE_2$ in microglia can promote neuroinflammation in several models of neurodegenerative diseases. The effect of EP2 antagonist compounds were examined on NMDA-induced excitotoxicity. Rat primary hippocampal cultures (DIV 13-15) were preincubated with vehicle or increasing concentrations of test compound for 15-20 min, followed by treatment with NMDA (30 μM) plus glycine (10 μM) overnight in continued presence of the test compound. Lactate dehydrogenase (LDH) release was used as the measure of neuronal injury. NMDA treatment induced a significant increase of LDH release in the rat hippocampal cultures, which was attenuated in a concentration-dependent manner by preincubation with these EP2 antagonist compounds. The NMDA-induced LDH release was reduced to 94.0, 87.8, 73.9, and 50.8% by 0.01, 0.1, 1, and 10 μM compound A1, respectively.

In addition, compounds A2, 1f, 1h, 1v, 1w and B1 were selected for this in vitro neuroprotection because of their low $K_B$s, high therapeutic and selectivity indexes, or desirable pharmacokinetics (PK) profile. The NMDA-induced LDH release was also reduced to 77.8, 38.5, 72.0, 49.9, 78.4, and 84.7% by compounds A2, 1f, 1h, 1v, 1w, and B1 at 10 μM, respectively. Consistently, the EP2-inactive analog 1e did not show any effect on NMDA-induced LDH release. Interestingly, compound A1 $EC_{50}$ for the reduction of NMDA-induced LDH release was 0.80 μM, so about 450-fold rightward shift in the $PGE_2$ concentration-response curve was required to yield half-maximal neuroprotection by the EP2 inhibition.

Microglia are the initial and major mediators of neuroinflammation and neurodegeneration in various models of neurological disorders. EP2 receptor has been reported to regulate microglial activation and subsequent neurotoxicity in several animal models. The effects of EP2 activation in microglia were investigated. Rat microglia-enriched cultures were incubated with vehicle, butaprost, or compound A 1 overnight. The cellular viability was evaluated by measuring Lactate dehydrogenase (LDH) release. Butaprost (10 μM) significantly increased LDH release to 138% in rat microglia-enriched cultures. On the contrary, EP2 antagonist compound A1 (10 μM) had no significant effect on basal LDH release in rat microglia-enriched cultures.

Certain Compounds Block EP2-Regulated Inflammation in Microglia

Nitric oxide (NO) synthesized by iNOS and prostaglandins produced by COX-2 are effectors of neurotoxicity and neuroinflammation, thus, these two inducible enzymes have been recognized as inflammatory mediators produced in activated microglia. As the dominant enzymatic product of COX-2, PGE$_2$ therefore might play a role in microglia-mediated neuroinflammation and neurodegeneration. To investigate this possibility, rat microgliaenriched cultures were preincubated with vehicle or increasing concentrations of compound A1, followed by treatment with 1 µM butaprost. Gene expression of a number of inflammatory mediators and cytokines were measured by quantitative real time polymerase chain reaction (qRT-PCR). EP2 activation by butaprost increased iNOS, COX-2, IL-1β and IL-6 expression by 3.4-, 16.3-, 1.8- and 11.1-fold, respectively, without affecting expression of the EP2 receptor itself. The upregulation of these inflammatory genes by butaprost was inhibited by preincubation with EP2 antagonist compound A 1 in a concentration-dependent manner. These data suggest that EP2 activation in microglia contributes to neuroinflammation possibly via upregulating inflammatory mediators including iNOS and COX-2.

Certain Compounds Reduce Weight Loss, Prevent Blood-Brain Barrier Destruction, and Reduce Neuroinflammation and Neurodegeneration in Hippocampus after Status Epilepticus.

COX-2 induction in CNS overall contributes to neuroinflammation and neurodegeneration by producing prostaglandins. However, the detailed downstream COX-2 signaling pathways involved in brain injury are not fully understood mainly because of the lack of selective small-molecule modulators for some prostaglandin receptors. Three doses of compound 1h were administered (5 mg/kg, IP) at 3, 10 and 30 hours after 1 hour of pilocarpine-induced status epilepticus. Status epilepticus caused a substantial weight loss of the animals, which was reduced by compound 1h by day 4 (P<0.001). Animals received 1h gained weight from day 1 to day 4 compared to animals received vehicle after status epileptics (P<0.01). The SE-induced mortality rate by day 4 was also reduced by compound 1h (p=0.034). Neuronal COX-2 induction after SE was demonstrated to regulate breakdown of the blood brain barrier (BBB). Compound 1h significantly prevented leakage of plasma albumin into the cortex four days after SE, measured by Western blot analysis (P<0.05), which suggests that EP2 activation might be involved in SE-induced BBB destruction.

Neuroinflammation and neurodegeneration are two prominent features following seizure-promoted COX-2 induction. The mRNA levels of cytokines—IL-1β, IL-6, TNFα and chemokines—CCL2, CCL3, CCL4, CXCL10 in hippocampi from mice received vehicle or compound 1h four days after SE were measured by quantitative real-time polymerase chain reaction (qRT-PCR). All seven cytokines and chemokines were substantially induced by SE and administration of 1h largely blunted the induction by an average of 54% (P<0.05). Pilocarpine-induced status epilepticus caused substantial neurodegeneration in hippocampus four days after status epilepticus. Administration of compound 1h significantly reduced the status epilepticus-induced neurodegeneration by 66% (P<0.05) in CA1, by 52% in CA3, and by 55% (P<0.01) in hilus. These results suggest the EP2 receptor is involved in COX-2-regulated neuroinflammation and neurodegeneration following a seizure.

What is claimed:

1. A pharmaceutical composition comprising a compound of Formula IC,

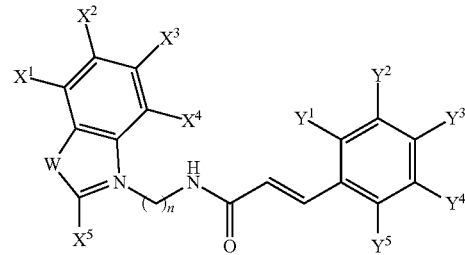

Formula IC or pharmaceutically acceptable salt or prodrug thereof, wherein:
W is CH or N;
n is 1, 2, 3, or 4;
$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
$X^5$ is alkyl, wherein $X^5$ is optionally substituted with one or more, the same or different, halogen.

2. The composition of claim 1, wherein n is 2.

3. A compound of Formula IC as in claim 1, selected from the group consisting of:
N-(2-(2-methyl-1H-indol-1-yl)ethyl)-3-(3,4,5-trimethoxyphenyl)acrylamide,
3-(3,4-dimethoxyphenyl)-N-(2-(2-methyl-1H-indol-1-yl)ethyl)acrylamide,
N-(2-(2-methyl-1H-benzo[d]imidazol-1-yl)ethyl)-3-(3,4,5-trimethoxyphenyl)acrylamide,
3-(3,4-dimethoxyphenyl)-N-(2-(2-methyl-1H-benzo[d]imidazol-1-yl)ethyl)acrylamide,
3-(benzo[d][1,3]dioxol-5-yl)-N-(2-(2-methyl-1H-benzo[d]imidazol-1-yl)ethyl)acrylamide,
N-(2-(5-fluoro-2-methyl-1H-indol-1-yl)ethyl)-3-(3,4,5-trimethoxyphenyl)acrylamide,
3-(3,4-dimethoxyphenyl)-N-(2-(5-fluoro-2-methyl-1H-indol-1-yl)ethyl)acrylamide,
N-(2-(5-fluoro-2-(trifluoromethyl)-1H-indol-1-yl)ethyl)-3-(3,4,5-trimethoxyphenyl)acrylamide,
3-(3,4-dimethoxyphenyl)-N-(2-(5-fluoro-2-(trifluoromethyl)-1H-indol-1-yl)ethyl)acrylamide,
N-(3-(2-methyl-1H-indol-1-yl)propyl)-3-(3,4,5-trimethoxyphenyl)acrylamide,
N-methyl-N-(2-(2-methyl-1H-indol-1-yl)ethyl)-3-(3,4,5-trimethoxyphenyl)acrylamide,
3-(4-methoxyphenyl)-N-(2-(2-methyl-1H-indol-1-yl)ethyl)acrylamide,
N-(2-(5-fluoro-2-methyl-1H-indol-1-yl)ethyl)-3-(4-methoxyphenyl)acrylamide,
3-(benzo[d][1,3]dioxol-5-yl)-N-(2-(2-methyl-1H-indol-1-yl)ethyl)acrylamide,
3-(4-ethoxy-3-methoxyphenyl)-N-(2-(2-methyl-1H-indol-1-yl)ethyl)acrylamide,
3-(4-isobutylphenyl)-N-(2-(2-methyl-1H-indol-1-yl)ethyl)acrylamide,
3-(3,4-difluorophenyl)-N-(2-(2-methyl-1H-indol-1-yl)ethyl)acrylamide, 3-(3,4-difluorophenyl)-N-(2-(5-fluoro-2-methyl-1H-indol-1-yl)ethyl)acrylamide,
N-(2-(2-methyl-1H-indol-1-yl)ethyl)-3-(3,4,5-trifluorophenyl)acrylamide,
N-(2-(5-fluoro-2-methyl-1H-indol-1-yl)ethyl)-3-(3,4,5-trifluorophenyl)acrylamide,
3-(3-bromo-4,5-dimethoxyphenyl)-N-(2-(5-fluoro-2-methyl-1H-indol-1-yl)ethyl)acrylamide,
3-(4-chloro-3-methoxyphenyl)-N-(2-(2-methyl-1H-indol-1-yl)ethyl)acrylamide,
3-(4-chloro-3-methoxyphenyl)-N-(2-(5-fluoro-2-methyl-1H-indol-1-yl)ethyl)acrylamide,
3-(5-bromo-2,4-dimethoxyphenyl)-N-(2-(2-methyl-1H-indol-1-yl)ethyl)acrylamide,
N-(2-(2-(trifluoromethyl)-1H-indol-1-yl)ethyl)-3-(3,4,5-trimethoxyphenyl)acrylamide,
3-(3,5-dimethoxyphenyl)-N-(2-(2-methyl-1H-indol-1-yl)ethyl)acrylamide,
3-(4-fluoro-3,5-dimethylphenyl)-N-(2-(2-(trifluoromethyl)-1H-indol-1-yl)ethyl)acrylamide, and
3-(4-fluoro-3,5-dimethylphenyl)-N-(2-(2-methyl-1H-indol-1-yl)ethyl)acrylamide or salts thereof.

\* \* \* \* \*